(12) United States Patent
Uchida et al.

(10) Patent No.: US 8,969,522 B2
(45) Date of Patent: Mar. 3, 2015

(54) METHOD FOR PRODUCING COLLAGEN-LIKE POLYPEPTIDE

(71) Applicant: JNC Corporation, Tokyo (JP)

(72) Inventors: Akihiro Uchida, Yokohama (JP); Shuji Sasaki, Yokohama (JP); Akiko Shimatani, Yokohama (JP); You Umebayashi, Moriyama (JP); Kazushi Ishida, Ichihara (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 13/929,805

(22) Filed: Jun. 28, 2013

(65) Prior Publication Data

US 2014/0128573 A1    May 8, 2014

(30) Foreign Application Priority Data

Jun. 29, 2012 (JP) ................................ 2012-146685

(51) Int. Cl.
*A61K 38/17* (2006.01)
*C07K 14/78* (2006.01)

(52) U.S. Cl.
CPC ..................................... *C07K 14/78* (2013.01)
USPC ...................................................... 530/356

(58) Field of Classification Search
None
See application file for complete search history.

(56) References Cited

U.S. PATENT DOCUMENTS

2010/0022755 A1* 1/2010 Umeda et al. ................ 530/381

FOREIGN PATENT DOCUMENTS

JP    2003-321500    11/2003
WO   2008075589     6/2008

OTHER PUBLICATIONS

Shumpei Sakakibara et al., "Synthesis of (Pro-Hyp-Gly)n of defined molecular weights, Evidence for the stabilization of collagen triple helix by hydroxypyroline," Biochimica et Biophysica Acta, 303, Mar. 23, 1973, pp. 198-202.
Takahiro Kishimoto et al., "Synthesis of Poly(Pro-Hyp-Gly)n by Direct Polycondensation of (Pro-Hyp-Gly)n, Where n=1,5, and 10, and Stability of the Triple-Helical Structure," Biopolymers, Aug. 10, 2005, vol. 79, pp. 163-172.

* cited by examiner

*Primary Examiner* — Suzanne M Noakes
(74) *Attorney, Agent, or Firm* — Jianq Chyun IP Office

(57) ABSTRACT

An object is to provide a method for producing an ever-larger molecular weight collagen-like polypeptide single strand. Another object is to provide a method for controlling a molecular weight of a product to be obtained in desired magnitude upon producing a collagen-like polypeptide single strand. A solution is a method for producing a polypeptide including a step for allowing a condensation reaction of peptide oligomers represented by any one of formulas (1) to (3) (SEQ ID No:1 to SEQ ID No:3), wherein the condensation reaction is carried out in an aqueous solvent containing a phosphate ion in the range of 0 M to less than 0.01 M in the presence of a condensing agent, or a condensing agent and a condensing auxiliary:

$$H\text{-}(Pro\text{-}Y\text{-}Gly)_n\text{-}OH \qquad (1);$$

$$H\text{-}(Y\text{-}Gly\text{-}Pro)_n\text{-}OH \qquad (2); \text{ and}$$

$$H\text{-}(Gly\text{-}Pro\text{-}Y)_n\text{-}OH \qquad (3);$$

wherein, in formulas (1) to (3), Y is hydroxyproline or proline, and n is an integer from 1 to 10.

4 Claims, 3 Drawing Sheets

METHOD FOR PRODUCING COLLAGEN-LIKE POLYPEPTIDE

CROSS-REFERENCE TO RELATED APPLICATIONS

This application claims the priority benefit of Japan application serial no. 2012-146685, filed on Jun. 29, 2012. The entirety of the above-mentioned patent application is hereby incorporated by reference herein and made a part of this specification.

TECHNICAL FIELD

The present invention relates to a method for producing a collagen-like polypeptide.

DESCRIPTION OF THE RELATED ART

A collagen being one kind of protein is broadly used as a general-purpose biomedical material. A naturally occurring type 1 collagen molecule has a characteristic primary structure formed of repetitions of three amino acid residues Gly-X-Y (wherein, X and Y represent various kinds of amino acids, and X is Pro, and Y is Hyp in many cases). Such a polypeptide takes a tertiary structure of a triple helix formed of three polypeptide fragments assembled in an identical direction to form a collagen fiber.

Meanwhile, a polypeptide molecule formed of a structure of repetitions of three amino acid residues Pro-Y-Gly (wherein, Y is proline or hydroxyproline), which is created as a collagen-like polypeptide (so-called synthetic collagen), is also reported to take a triple helical structure (Non-patent literature Nos. 1 to 2).

The collagen-like polypeptide, as is different from a naturally occurring collagen, has various excellent properties such as no risk of an infectious disease, a capability of stable supply because the collagen can be obtained by industrial synthesis, a high thermal stability of the triple helical structure, and no coloring and no odor. Therefore, a study has been conducted as various functional materials (Patent literature No. 1 or the like).

Ordinarily, a collagen-like polypeptide single strand is produced by a condensation reaction of peptide oligomers including fragments represented by -(Pro-Y-Gly)$_n$- (wherein, Y is Hyp or Pro). For example, Patent literature No. 2 describes a method for allowing peptide oligomers including peptide fragments represented by -(Pro-Y-Gly)$_n$- (wherein, Y is Hyp or Pro, and n=1 to 20) to polymerize by a condensation reaction in dimethylsulfoxide or in an aqueous solvent containing ethylenediamine.

However, when utilizing a collagen-like polypeptide complex as one of the functional materials, a drawback may be occasionally present in processability and physical properties of the complex.

For example, while a nanofiber has attracted attention as a material form in recent years, a conventional collagen-like polypeptide has had difficulty upon forming the nanofiber from the collagen-like polypeptide. More specifically, the collagen-like polypeptide that is different from the naturally occurring collagen molecule has a simple repetition structure consisting of Pro-Y-Gly. Therefore, the collagen-like polypeptide has poor interaction between molecular chains despite a macromolecular peptide, and even when spinning of the collagen-like polypeptide is tried in a single form, no fibrous polypeptide has been obtained due to thread breakage or formation of beads of the collagen-like polypeptide.

Moreover, for example, when the collagen-like polypeptide is used as a polymer material, the conventional collagen-like polypeptide has had insufficient mechanical strength.

The present inventors have first found that the problems are caused by magnitude of molecular weight of the collagen-like polypeptide single strand and the complex thereof, and have considered that the problems can be resolved by further increasing the molecular weight of the collagen-like polypeptide single strand and the complex thereof. However, no development has been made for a method for producing a desired molecular weight collagen-like polypeptide single strand, particularly, a high molecular weight collagen-like polypeptide single strand.

A specific reason therefor includes significant difficulty in investigating an accurate molecular weight because the collagen-like polypeptide complex forms a huge aggregate structure. Under such a situation, even if controlling of a molecular weight of a product to be obtained is tried, an evaluation of the molecular weight is difficult, and thus a problem of no progress of development of a method for obtaining the desired molecular weight collagen-like polypeptide is produced, and a solution thereof is also desired.

CITATION LIST

Patent Literature

Patent literature No. 1: WO 2008/075589 A.
Patent literature No. 2: JP 2003-321500 A.

Non-Patent Literature

Non-patent literature No. 1: S. Sakakibara et al., Biochim. Biophys. Acta, 303, 198 (1973).
Non-patent literature No. 2: T. Kishimoto et al., Biopolymers, 79, 163-172 (2005).

SUMMARY OF INVENTION

More specifically, the invention concerns items as described below.

Item 1. A method for producing a polypeptide, including a step for allowing peptide oligomers represented by any one of formulas (1) to (3)(SEQ ID No:1 SEQ ID No:3) below to polymerize by a condensation reaction, wherein the condensation reaction is carried out in an aqueous solvent containing a phosphate ion in the range of 0 M or more to 0.1 less than 0.01 N in the presence of a condensation agent, or a condensation agent and a condensation auxiliary:

H-(Pro-Y-Gly)$_n$-OH      (1)(SEQ ID No:1);

H-(Y-Gly-Pro)$_n$-OH      (2)(SEQ ID No:2); and

H-(Gly-Pro-Y)$_n$-OH      (3)(SEQ ID No:3);

wherein, in formulas (1) to (3)(SEQ ID No:1 to SEQ ID No:3), Y is hydroxyproline or proline, and n is an integer from 1 to 10.

Item 2. A method for controlling a molecular weight of a product to be obtained by a condensation reaction of peptide oligomers represented by any one of formulas (1) to (3) (SEQ ID No:1 SEQ ID No:3)below in an aqueous solvent containing a phosphate ion, wherein a concentration of the phosphate ion is adjusted in the range of 0 to 0.2 M in the condensation reaction:

H-(Pro-Y-Gly)$_n$-OH      (1)(SEQ ID No:1);

H-(Y-Gly-Pro)$_n$-OH      (2)(SEQ ID No:2); and

H-(Gly-Pro-Y)$_n$-OH      (3)(SEQ ID No:3);

wherein, in formulas (1) to (3)(SEQ ID No:1 to SEQ ID No:3), Y is hydroxyproline or proline, and n is an integer from 1 to 10.

Item 3. A polypeptide having a peptide fragment represented by formula (4)(SEQ ID No:4) below:

$$-(\text{Pro-Y-Gly})_m- \qquad (4)(\text{SEQ ID No:4})$$

wherein, in formula (4)(SEQ ID No:4), Y is hydroxyproline or proline, and m is an integer from 100 to 171.

Item 4. The polypeptide according to item 3, wherein a weight average molecular weight of a single chain is in the range of 26,700 to 45,600.

Item 5. A nanofiber comprising the polypeptide according to item 3 or 4.

DESCRIPTION OF EMBODIMENTS

Figure 1:
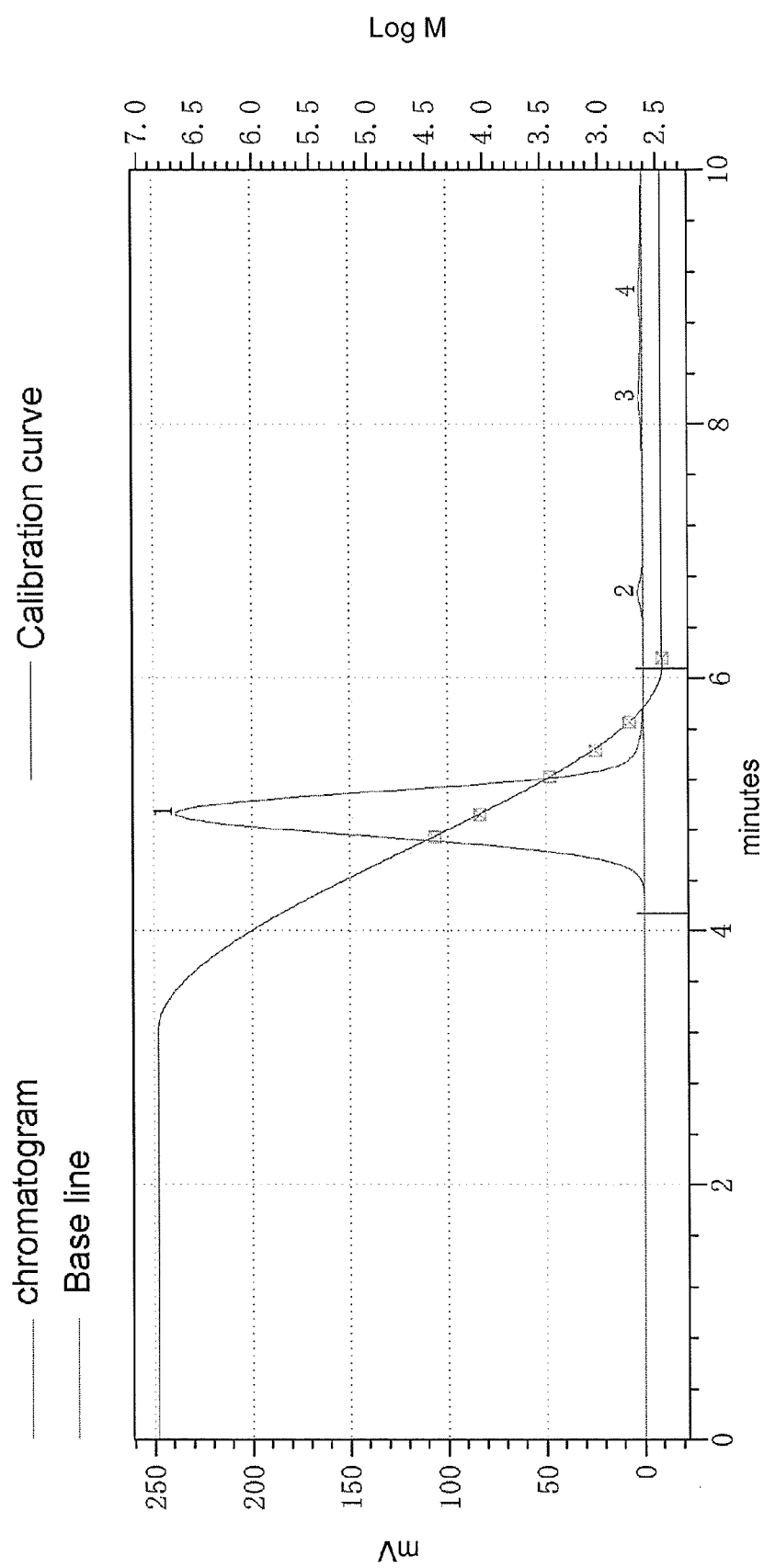
FIG. 1 shows an HFIP-based GPC measurement chart of a collagen-like polypeptide single strand.

In view of the situation described above, an object of the invention is to provide a method of producing an ever-higher molecular weight collagen-like polypeptide single strand. Another object of the invention is to provide a method for controlling a molecular weight of a product to be obtained in desired magnitude upon producing a collagen-like polypeptide single strand.

The present inventors have diligently continued to conduct research for solving the problem, and as a result, have found that a higher molecular weight collagen-like polypeptide can be produced, upon producing a collagen-like polypeptide by a condensation reaction of oligomers, by carrying out the reaction in an aqueous solvent and adjusting a phosphate ion concentration in the solvent.

According to the invention, a molecular weight of a collagen-like polypeptide to be formed can be controlled in desired magnitude by a simple and inexpensive means, and a means for obtaining an ever-higher molecular weight collagen-like polypeptide is provided. When collagen-like polypeptides having various levels of molecular weights, particularly, having a high molecular weight are obtained, processability of the polypeptide is significantly improved, and a width of an application as a functional material is extended.

"Collagen-like polypeptide single strand" herein means a polypeptide having a repetitive sequence of Pro-Y-Gly (wherein, Y is hydroxyproline or proline), and the polypeptide in a state present as one chain without taking a structure such as a triple helix by interaction between molecular chains. Moreover, "collagen-like polypeptide complex" represents a state in which the collagen-like polypeptide single strands take a triple helical structure. In many cases, in the collagen-like polypeptide complex, the triple helix further takes a branch structure or forms a high-order structure in which aggregation is caused among triple helical molecules. In addition, whether or not the collagen-like polypeptide single strands take the triple helical structure can be confirmed by measuring a circular dichroism spectrum as described later.

Various amino acid residues herein are described by means of abbreviations as described below.

Ala: L-alanine residue;
Arg: L-arginine residue;
Asn: L-asparagine residue;
Asp: L-aspartyl residue;
Cys: L-cysteine residue;
Gln: L-glutamine residue;
Glu: L-glutamate residue;
Gly: glycine residue;
His: L-histidine residue;
Hyp: L-hydroxyproline residue;
Ile: L-isoleucine residue;
Leu: L-leucine residue;
Lys: L-lysine residue;
Met: L-methionine residue;
Phe: L-phenylalanine residue;
Pro: L-proline residue;
Sar: sarcosine residue;
Ser: L-serine residue;
Thr: L-threonine residue;
Trp: L-tryptophan residue;
Tyr: L-tyrosine residue; and
Val: L-valine residue.

In addition, an amino acid sequence of peptide chains herein is described by drawing an N-terminus of an amino acid residue on a left-hand side and a C-terminus thereof on a right-hand side in accordance with an ordinary way.

(1) Method for Producing a Polypeptide According to the Invention

A method for producing a polypeptide according to the invention includes a step for allowing peptide oligomers represented by any one of formulas (1) to (3)(SEQ ID No:1 to SEQ ID No:3) below to polymerize by a condensation reaction:

$$\text{H-(Pro-Y-Gly)}_n\text{-OH} \qquad (1)(\text{SEQ ID No:1});$$

$$\text{H-(Y-Gly-Pro)}_n\text{-OH} \qquad (2)(\text{SEQ ID No:2}); \text{ and}$$

$$\text{H-(Gly-Pro-Y)}_n\text{-OH} \qquad (3)(\text{SEQ ID No:3});$$

In formulas (1) to (3)(SEQ ID No:1 to SEQ ID No:3), Y is hydroxyproline or proline, preferably, hydroxyproline. A specific example of hydroxyproline includes 4Hyp, and trans-4-hydroxy-L-proline is preferred. Moreover, n is an integer from 1 to 10, preferably, an integer from 1 to 5 in a viewpoint of ease of handling, efficiency of the condensation reaction, availability of a peptide oligomer and economic efficiency.

In the invention, as the peptide oligomers represented by formulas (1) to (3)(SEQ ID No:1 to SEQ ID No:3), any one of kinds of the peptide oligomers may be used, or a mixture thereof may also be used. Moreover, n may be a single integer or may be a mixture of oligomers having various types of the number of repetitions.

The peptide oligomers can be obtained by a known solid-phase synthesis process or liquid-phase synthesis process.

A peptide oligomer other than the peptide oligomers represented by formulas (1) to (3) (SEQ ID No:1 to SEQ ID No:3) may also be used. However, an amount of use of the peptide oligomers represented by formulas (1) to (3)(SEQ ID No:1 to SEQ ID No:3) and any other peptide oligomer is preferably in the range of approximately 100:0 to approximately 50:50 in a weight ratio. When the amount of use of any other peptide oligomer is in the range described above, the collagen-like polypeptide single strand to be produced easily forms the triple helical structure.

Specific examples of other peptide oligomers include peptide oligomers represented by formulas (5) to (68)(SEQ ID No:5 to SEQ ID No:68) below.

(Asp-Pro-Gly)$_o$ (5)(SEQ ID No:5)

(Asp-Hyp-Gly)$_o$ (6)(SEQ ID No:6)

(Glu-Pro-Gly)$_o$ (7)(SEQ ID No:7)

(Glu-Hyp-Gly)$_o$ (8)(SEQ ID No:8)

(Pro-Gln-Gly-Ile-Ala-Gly)$_o$ (9)(SEQ ID No:9)

(Pro-Asn-Gly-Ile-Ala-Gly)$_o$ (10)(SEQ ID No:10)

(Pro-Leu-Gly-Ile-Ala-Gly)$_o$ (11)(SEQ ID No:11)

(Pro-Ile-Gly-Ile-Ala-Gly)$_o$ (12)(SEQ ID No:12)

(Pro-Val-Gly-Ile-Ala-Gly)$_o$ (13)(SEQ ID No:13)

(Pro-Ala-Gly-Ile-Ala-Gly)$_o$ (14)(SEQ ID No:14)

(Pro-Gln-Gly-Leu-Ala-Gly)$_o$ (15)(SEQ ID No:15)

(Pro-Asn-Gly-Leu-Ala-Gly)$_o$ (16)(SEQ ID No:16)

(Pro-Leu-Gly-Leu-Ala-Gly)$_o$ (17)(SEQ ID No:17)

(Pro-Ile-Gly-Leu-Ala-Gly)$_o$ (18)(SEQ ID No:18)

(Pro-Val-Gly-Leu-Ala-Gly)$_o$ (19)(SEQ ID No:19)

(Pro-Ala-Gly-Leu-Ala-Gly)$_o$ (20)(SEQ ID No:20)

(Asp-Pro-Gly)$_p$-(Pro-Gln-Gly-Ile-Ala-Gly)$_q$ (21)(SEQ ID No:21)

(Asp-Pro-Gly)$_p$-(Pro-Asn-Gly-Ile-Ala-Gly)$_q$ (22)(SEQ ID No:22)

(Asp-Pro-Gly)$_p$-(Pro-Leu-Sly-Ile-Ala-Gly)$_q$ (23)(SEQ ID No:23)

(Asp-Pro-Gly)$_p$-(Pro-Ile-Gly-Ile-Ala-Gly)$_q$ (24)(SEQ ID No:24)

(Asp-Pro-Gly)$_p$-(Pro-Val-Gly-Ile-Ala-Gly)$_q$ (25)(SEQ ID No:25)

(Asp-Pro-Gly)$_p$-(Pro-Ala-Gly-Ile-Ala-Gly)$_q$ (26)(SEQ ID No:26)

(Asp-Pro-Gly)$_p$-(Pro-Gln-Gly-Leu-Ala-Gly)$_q$ (27)(SEQ ID No:27)

(Asp-Pro-Gly)$_p$-(Pro-Asn-Gly-Leu-Ala-Gly)$_q$ (28)(SEQ ID No:28)

(Asp-Pro-Gly)$_p$-(Pro-Leu-Gly-Leu-Ala-Gly)$_q$ (29)(SEQ ID No:29)

(Asp-Pro-Gly)$_p$-(Pro-Ile-Gly-Leu-Ala-Gly)$_q$ (30)(SEQ ID No:30)

(Asp-Pro-Gly)$_p$-(Pro-Val-Gly-Leu-Ala-Gly)$_q$ (31)(SEQ ID No:31)

(Asp-Pro-Gly)$_p$-(Pro-Ala-Gly-Leu-Ala-Gly)$_q$ (32)(SEQ ID No:32)

(Asp-Hyp-Gly)$_p$-(Pro-Gln-Gly-Ile-Ala-Gly)$_q$ (33)(SEQ ID No:33)

(Asp-Hyp-Gly)$_p$-(Pro-Asn-Gly-Ile-Ala-Gly)$_q$ (34)(SEQ ID No:34)

(Asp-Hyp-Gly)$_p$-(Pro-Leu-Gly-Ile-Ala-Gly)$_q$ (35)(SEQ ID No:35)

(Asp-Hyp-Gly)$_p$-(Pro-Ile-Gly-Ile-Ala-Gly)$_q$ (36)(SEQ ID No:36)

(Asp-Hyp-Gly)$_p$-(Pro-Val-Gly-Ile-Ala-Gly)$_q$ (37)(SEQ ID No:37)

(Asp-Hyp-Gly)$_p$-(Pro-Ala-Gly-Ile-Ala-Gly)$_q$ (38)(SEQ ID No:38)

(Asp-Hyp-Gly)$_p$-(Pro-Gln-Gly-Leu-Ala-Gly)$_q$ (39)(SEQ ID No:39)

(Asp-Hyp-Gly)$_p$-(Pro-Asn-Gly-Leu-Ala-Gly)$_q$ (40)(SEQ ID No:40)

(Asp-Hyp-Gly)$_p$-(Pro-Leu-Gly-Leu-Ala-Gly)$_q$ (41)(SEQ ID No:41)

(Asp-Hyp-Gly)$_p$-(Pro-Ile-Gly-Leu-Ala-Gly)$_q$ (42)(SEQ ID No:42)

(Asp-Hyp-Gly)$_p$-(Pro-Val-Gly-Leu-Ala-Gly)$_q$ (43)(SEQ ID No:43)

(Asp-Hyp-Gly)$_p$-(Pro-Ala-Gly-Leu-Ala-Gly)$_q$ (44)(SEQ ID No:44)

(Glu-Pro-Gly)$_p$-(Pro-Gln-Gly-Ile-Ala-Gly)$_q$ (45)(SEQ ID No:45)

(Glu-Pro-Gly)$_p$-(Pro-Asn-Gly-Ile-Ala-Gly)$_q$ (46)(SEQ ID No:46)

(Glu-Pro-Gly)$_p$-(Pro-Leu-Gly-Ile-Ala-Gly)$_q$ (47)(SEQ ID No:47)

(Glu-Pro-Gly)$_p$-(Pro-Ile-Gly-Ile-Ala-Gly)$_q$ (48)(SEQ ID No:48)

(Glu-Pro-Gly)$_p$-(Pro-Val-Gly-Ile-Ala-Gly)$_q$ (49)(SEQ ID No:49)

(Glu-Pro-Gly)$_p$-(Pro-Ala-Gly-Ile-Ala-Gly)$_q$ (50)(SEQ ID No:50)

(Glu-Pro-Gly)$_p$-(Pro-Gln-Gly-Leu-Ala-Gly)$_q$ (51)(SEQ ID No:51)

(Glu-Pro-Gly)$_o$-(Pro-Asn-Gly-Leu-Ala-Gly)$_q$ (52)(SEQ ID No:52)

(Glu-Pro-Gly)$_p$-(Pro-Leu-Gly-Leu-Ala-Gly)$_q$ (53)(SEQ ID No:53)

(Glu-Pro-Gly)$_p$-(Pro-Ile-Gly-Leu-Ala-Gly)$_q$ (54)(SEQ ID No:54)

(Glu-Pro-Gly)$_p$-(Pro-Val-Gly-Leu-Ala-Gly)$_q$ (55)(SEQ ID No:55)

(Glu-Pro-Gly)$_p$-(Pro-Ala-Gly-Leu-Ala-Gly)$_q$ (56)(SEQ ID No:56)

(Glu-Hyp-Gly)$_p$-(Pro-Gln-Gly-Ile-Ala-Gly)$_q$ (57)(SEQ ID No:57)

(Glu-Hyp-Gly)$_p$-(Pro-Asn-Gly-Ile-Ala-Gly)$_q$ (58)(SEQ ID No:58)

(Glu-Hyp-Gly)$_p$-(Pro-Leu-Gly-Ile-Ala-Gly)$_q$ (59)(SEQ ID No:59)

(Glu-Hyp-Gly)$_p$-(Pro-Ile-Gly-Ile-Ala-Gly)$_q$ (60)(SEQ ID No:60)

(Glu-Hyp-Gly)$_p$-(Pro-Val-Gly-Ile-Ala-Gly)$_q$ (61)(SEQ ID No:61)

(Glu-Hyp-Gly)$_p$-(Pro-Ala-Gly-Ile-Ala-Gly)$_q$ (62)(SEQ ID No:61)

(Glu-Hyp-Gly)$_p$-(Pro-Gln-Gly-Leu-Ala-Gly)$_q$ (63)(SEQ ID No:63)

(Glu-Hyp-Gly)$_p$-(Pro-Asn-Gly-Leu-Ala-Gly)$_q$ (64)(SEQ ID No:64)

(Glu-Hyp-Gly)$_p$-(Pro-Leu-Gly-Leu-Ala-Gly)$_q$ (65)(SEQ ID No:65)

(Glu-Hyp-Gly)$_p$-(Pro-Ile-Gly-Leu-Ala-Gly)$_q$ (66)(SEQ ID No:66)

(Glu-Hyp-Gly)$_p$-(Pro-Val-Gly-Leu-Ala-Gly)$_q$ (67)(SEQ ID No:67)

(Glu-Hyp-Gly)$_p$-(Pro-Ala-Gly-Leu-Ala-Gly)$_q$ (68)(SEQ ID No:68)

In formulas (5) to (20)(SEQ ID No:5 to SEQ ID No:20), o is an integer from 1 to 10, and in formulas (21) to (68)(SEQ ID No:21 to SEQ ID No:68), p is an integer from 1 to 10, and q is an integer from 1 to 10. However, in view of efficiency of the condensation reaction, and availability of the peptide oligomer, o, p and q are independently preferably an integer from 1 to 5, particularly preferably, 1.

The condensation reaction in the production method according to the invention is carried out in the aqueous solvent containing the phosphate ion.

In the invention, the aqueous solvent means a water-containing solvent, or an aqueous solvent in which an organic solvent may be mixed. Here, the organic solvent means amides (dimethylformamide, dimethylacetamide, hexamethylphosphoroamide or the like), sulfoxide (dimethylsulfoxide or the like), a nitrogen-containing cyclic compound (N-methylpyrrolidone, pyridine or the like), nitriles (acetonitrile or the like), ethers (dioxane, tetrahydrofuran or the like) and alcohols (methyl alcohol, ethyl alcohol, propyl alcohol or the like). Moreover, an expression "may be mixed" means that the content is preferably less than approximately 50% by weight, further preferably, less than approximately 10% by weight, still further preferably, none at all.

In the invention, the phosphate ion is a generic term for a dihydrogenphosphate ion ($H_2PO_4^-$), a hydrogen phosphate ion ($HPO_4^{2-}$) and a phosphate ion ($PO_4^{3-}$), and a phosphate ion concentration in the aqueous solvent is expressed in terms of a total concentration of the dihydrogenphosphate ion ($H_2PO_4^-$), the hydrogen phosphate ion ($HPO_4^{2-}$) and the phosphate ion ($PO_4^{3-}$)

If the phosphate ion concentration in the aqueous solvent is decreased, a high molecular weight collagen-like polypeptide single strand can be produced, and if the concentration is increased, a low molecular weight collagen-like polypeptide single strand can be produced. When the phosphate ion concentration is adjusted, a molecular weight of a collagen-like polypeptide single strand to be produced can be controlled.

Specifically, the invention will be explained by taking as an example a case where the concentration of the peptide oligomer in the aqueous solvent is 5% by weight. In a case where the phosphate ion concentration is approximately 0 to approximately 0.0025 M, a collagen-like polypeptide single strand having a weight average molecular weight in the range of approximately 45,600 to approximately 26,700 is obtained. In a case where the concentration is in the range of approximately 0.005M to less than approximately 0.01 M, a collagen-like polypeptide single strand in the range of approximately 20,300 to approximately 16,000 is obtained. Thus, a high molecular weight collagen-like polypeptide single strand that has been difficult to obtain so far can be produced. Moreover, when the concentration is in the range of approximately 0.012 to approximately 0.06 M, a collagen-like polypeptide single strand having a weight average molecular weight in the range of approximately 13,500 to approximately 7,100 is obtained.

The phosphate ion concentration can be adjusted by adding phosphate such as potassium dihydrogenphosphate and disodium hydrogenphosphate to the aqueous solvent. The phosphates can be obtained simply and inexpensively, and regulation of the concentration is also simple, and therefore the invention can be easily carried out.

In the condensation reaction according to the invention, the concentration of the peptide oligomer in the aqueous solvent is preferably in the range of approximately 0.1 to approximately 50% by weight from a viewpoint of reaction efficiency, further preferably, in the range of approximately 4 to approximately 25% by weight from a viewpoint of handling of the reaction. In addition, when the concentration of the peptide oligomer is decreased, the molecular weight of the collagen-like polypeptide single strand to be formed can also be controlled to be small.

Moreover, from a viewpoint of reaction efficiency, a temperature at which the condensation reaction is carried out is preferably in the range of approximately 0 to approximately 60° C., further preferably, in the range of approximately 4 to approximately 20° C.

Moreover, reaction time is preferably in the range of approximately 1 to approximately 96 hours, further preferably, in the range of approximately 2 to approximately 48 hours.

Moreover, pH of the aqueous solvent upon carrying out the condensation reaction is not particularly limited, but is ordinarily adjusted to a vicinity of neutrality (pH=approximately 6 to approximately 8). Adjustment of pH can be ordinarily carried out using an inorganic base (sodium hydroxide, potassium hydroxide, sodium carbonate, sodium hydrogencarbonate or the like), an organic base, an inorganic acid (hydrochloric acid or the like) or an organic acid.

In order to improve reaction efficiency, the aqueous solvent may also be stirred, which is not particularly limited.

Moreover, the condensation reaction in the production method according to the invention is carried out in the presence of a dehydration agent (a dehydration-condensation agent or a condensation auxiliary). In the presence of the dehydration agent, the condensation reaction smoothly progresses, while suppressing dimerization or cyclization, without passing through complicated treatment in which deprotection and amino acid bonding are repeated.

The dehydration-condensation agent is not particularly limited, as long as dehydration condensation can be efficiently performed in the solvent. Specific examples include a carbodiimide condensation agent (diisopropylcarbodiimide (DIPC), 1-ethyl-3-(3-dimethylaminopropyl)-carbodiimide (EDC=WSCI), 1-ethyl-3-(3-dimethylaminopropyl)-carbodiimide hydrochloride (WSCI.HCl) or dicyclohexylcarbodiimide (DCC)), a fluorophosphate condensation agent (O-(7-azabenzotriazole-1-yl)-1,1,3,3-tetramethyluronium hexafluorophosphate, O-benzotriazole-1-yl-N,N,N',N'-tetramethyluronium hexafluorophosphate, benzotriazole-1-yl-oxy-tris-pyrrolidinophosphonium hexafluorophosphate, benzotriazole-1-yl-tris(dimethylamino)phosphonium hexafluorophosphate (BOP)) or diphenylphosphoryl azide (DPPA).

The dehydration-condensation agents can be used alone or in the form of a mixture in combination with two or more kinds. A preferred dehydration-condensation agent includes a carbodiimide condensation agent (1-ethyl-3-(3-dimethylaminopropyl)-carbodiimide or 1-ethyl-3-(3-dimethylaminopropyl)-carbodiimide hydrochloride, for example).

When a non-aqueous solvent containing no water is used, an amount of use of the dehydration-condensation agent is ordinarily in the range of approximately 0.7 to approximately 5 mol, preferably, in the range of approximately 0.8 to approximately 2.5 mol, further preferably, in the range of approximately 0.9 to approximately 2.3 mol (approximately 1 to approximately 2 mol, for example), based on 1 mol of the total amount of the peptide oligomers. In a water-containing solvent (aqueous solvent), inactivation of the dehydration-condensation agent by water is caused. Therefore, an amount of use of the dehydration-condensation agent is ordinarily in the range of approximately 2 to approximately 500 mol, preferably, in the range of approximately 5 to approximately 250 mol, further preferably, in the range of approximately 10 to approximately 125 mol, based on 1 mol of the total amount of the peptide oligomers.

The condensation auxiliary is not particularly limited, as long as the condensation auxiliary promotes the condensation reaction. Specific examples include N-hydroxy polycarboxylic imides (N-hydroxy dicarboxylic imides such as N-hydroxysuccinimide (HONSu) and N-hydroxy-5-norbornene-2,3-dicarboxylic imide (HONG)), N-hydroxytriazoles (N-hydroxybenzotriazoles such as 1-hydroxybenzotriazole (HOBt)), triazines such as 3-hydroxy-4-oxo-3,4-dihydro-1, 2,3-benzotriazine (HOObt) or 2-hydroxyimino-2-cyanoacetic acid ethyl ester.

The condensation auxiliaries can also be used alone or in combination with two or more kinds. A preferred condensation auxiliary includes N-hydroxy dicarboxylic imides (HONSu), N-hydroxybenzotriazole or N-hydroxybenzotriazines (HOBt).

An amount of use of the condensation auxiliary is ordinarily in the range of approximately 0.5 to approximately 5 mol, preferably, in the range of approximately 0.7 to approximately 2 mol, further preferably, in the range of approximately 0.8 to approximately 1.5 mol, based on 1 mol of the total amount of the peptide oligomers, regardless of kinds of solvents.

In the invention, the dehydration-condensation agent only may be used, but the dehydration-condensation agent and the condensation auxiliary are preferably suitably combined and used. Specific examples of combinations of the dehydration-condensation agent and the condensation auxiliary include a combination of DCC and HONSu (HOBt or HOOBt) or a combination of WSCI and HONSu (HOBt or HOOBt).

The polypeptide obtained by the production method according to the invention is formed into powder by freeze drying, or the like, and can be processed into a form that is easily handled for provision for subsequent processing. When carrying out freeze drying, a reaction mixture after the condensation reaction is put into a suitable vessel such as a recovery flask, and freeze drying is carried out using a freeze dryer (EYELA FDU-2000, made by Tokyo Rikakikai Co., Ltd., for example). Freeze drying is carried out until moisture evaporates and a dry matter is obtained, and ordinarily completed overnight to in two days. When the dry matter obtained is dissolved into an arbitrary solvent at a desired concentration, a stock solution for provision for production of a fiber, a nanofiber, a gel or the like can be prepared.

Moreover, a reagent used for the reaction remains in the polypeptide obtained according to the production method of the invention. The reagent may possibly affect the polypeptide when the polypeptide obtained is subsequently provided for processing or the like, and therefore is preferably removed. Removal of the remaining reagent can be performed by using a known technique such as dialysis, a column process and an ultrafiltration process.

Moreover, a reaction solvent is preferably replaced by a storage solvent in view of stability and ease of handling of the polypeptide. Replacement from the reaction solvent to an object storage solvent can be performed by using the object solvent as a dialysis supplement buffer in the dialysis, or using the object storage solvent as a mobile phase in the column process.

The storage solvent is not particularly limited, if the storage solvent can suppress a change of physical properties and so forth of the polypeptide obtained. Specific examples include water, a physiological salt solution and a buffer having buffer capacity from weak acid to weak alkali.

(2) Polypeptide of the Invention

The polypeptide of the invention includes the collagen-like polypeptide single strand having a peptide fragment (hereinafter, described as polyPYG) represented by formula (4) (SEQ ID No:4) below:

-(Pro-Y-Gly)$_m$-     (4)(SEQ ID No:4)

wherein, Y is hydroxyproline or proline, and a specific example of hydroxyproline includes 4Hyp, and trans-4-hydroxy-L-proline is preferred.

Moreover, in formula (4)(SEQ ID No:4), the number of repetition m is an integer from 100 to 171. More specifically, as compared with a conventional collagen-like polypeptide single strand, the number of repetitions is larger.

Moreover, the weight average molecular weight of the polypeptide according to the invention is in the range of approximately 26,700 to approximately 45,600 per single chain. More specifically, the polypeptide includes a higher molecular weight polypeptide in comparison with the collagen-like polypeptide single strand that has been synthesized so far. In addition, such a weight average molecular weight is expressed in terms of a value measured by HFIP-based GPC as described later.

The polypeptide single chain of the invention takes the triple helical structure as in a naturally occurring collagen, and can form the collagen-like polypeptide complex. In addition, whether or not the polypeptide takes the triple helical structure can be confirmed by measuring the circular dichroism spectrum of the polypeptide solution. Specifically, when the polypeptide shows a positive Cotton effect in a wavelength in the range of approximately 220 to approximately 230 nanometers and a negative Cotton effect in a wavelength in the range of approximately 195 to approximately 205 nanometers, the polypeptide is considered to take the triple helical structure.

The polypeptide of the invention may have a straight chain or one or more branches. When the polypeptide has a branch, the triple helical structure may be formed in and after a branch point, and may further have a branch behind the triple helical structure. Moreover, the polypeptide single chains may also be cross-linked with each other.

The collagen-like polypeptide single strand in the invention may consist of polyPYG, but may also include an amino acid residue, a peptide fragment or alkylene in addition to polyPYG.

Specific examples of the amino acid residues include at least one kind selected from Ala, Arg, Asn, Asp, Cys, Gln, Glu, Gly, His, Hyp, Ile, Leu, Lys, Met, Phe, Pro, Sar, Ser, Thr, Trp, Tyr and Val. A specific example of the peptide fragments includes a peptide in which pluralities of at least one kind of the amino acid residue are connected. Alkylene may be linear or branched, and is not particularly limited. A specific example includes alkylene having 1 to 18 carbons, and alkylene having 2 to 12 carbons is preferred for practical purpose.

The polypeptide single strand of the invention has PolyPYG, and any other amino acid residue, a peptide fragment or alkylene in a weight ratio in the range of PolyPYG:any other amino acid residue, a peptide fragment or alkylene=approximately 1:99 to approximately 100:0, preferably, in the range of approximately 10:90 to approximately 100:0.

The polypeptide of the invention has a molecular weight larger than the molecular weight of the conventional polypeptide in the form of the single chain, and therefore exhibits newer or superb properties as physical properties of the collagen-like polypeptide single strand or the complex. For example, when the collagen-like polypeptide turns into a gel, the mechanical strength is improved.

Moreover, the polypeptide has a high molecular weight, and thus fiber formation can be made in a single form, while a collagen-like polypeptide complex having a weight average molecular weight (single chain) in the range of approximately 3,000 to approximately 20,000 has been quite difficult to form fibers. The fibers comprising the polypeptide, particularly, the nanofibers according to the invention can be, as a functional material, provided for various applications such as a medical material. For example, the fibers can be applied to an adsorbent using high affinity of the collagen-like polypeptide complex with biomolecules such as a blood coagulation factor, or a haemostatic agent using blood coagulation ability.

As a method for forming the fibers, a well-known technique can be applied, and is not particularly limited. A specific example includes a technique for discharging into methanol using a syringe a solution prepared by dissolving the polypeptide of the invention into an organic solvent (hexafluoroisopropanol).

Moreover, a specific example includes a spinning process by an electrospinning process. If the electrospinning process is applied, uniform collagen-like polypeptide complex fibers each having a fiber diameter in the range of approximately 5 nanometers to approximately 50 micrometers can be obtained, and nanofibers each having a fiber diameter in a nanometer unit (approximately 1 to approximately 1,000 nanometers) can also obtained.

A method for spinning the fibers including the polypeptide of the invention (including the nanofibers of the invention) by the electrospinning process will be explained below.

First, the polypeptide of the invention is dissolved into a solvent to prepare a spinning solution. Such a solvent is not particularly limited, if the solvent dissolves the polypeptide, evaporates in a step for spinning the fibers to allow formation of the fibers. Specific examples include water, ethanol, methanol, isopropanol, acetone, sulfolane acetone, propanol, dichloromethane, formic acid, hexafluoroisopropanol, hexafluoroacetone, methyl ethyl ketone, chloroform, isopropanol, toluene, tetrahydrofuran, benzene, benzyl alcohol, 1,4-dioxane, carbon tetrachloride, cyclohexane, cyclohexanone, methylene chloride, phenol, pyridine, trichloroethane, acetic acid, N,N-dimethylformamide, dimethylsulfoxide, N,N-dimethylacetamide, 1-methyl-2-pyrrolidone, ethylene carbonate, propylene carbonate, dimethyl carbonate, acetonitrile, N-methylmorpholine-N-oxide, butylene carbonate, 1,4-butyrolactone, diethyl carbonate, diethyl ether, 1,2-dimethoxyethane, 1,3-dimethyl-2-imidazolidinone, 1,3-dioxolane, ethyl methyl carbonate, methylformate, 3-methyloxazolidine-2-one, methylpropionate and 2-methyltetrahydrofuran. The solvents may be used alone in one kind or may be used in the form of a mixture of a plurality of solvents.

In order to facilitate formation of continuous fibers, a polypeptide concentration in the spinning solution is preferably in the range of approximately 0.1 to approximately 10.0% by weight, further preferably, in the range of approximately 1.0 to approximately 8.0% by weight, still further preferably, in the range of approximately 3.0 to approximately 6.0% by weight.

Moreover, the polypeptide of the invention has a large molecular weight per single chain, and therefore can be spun in the single form, but a spinning solution may also be prepared simultaneously using any other polymer. In the case, mechanical strength of fibers obtained can be improved, a fiber length can be increased, or various functions can be given. Specific examples of other polymers include polyethylene glycol, polyvinyl alcohol, polypropylene and polystyrene, but are not particularly limited thereto.

Moreover, the spinning solution may contain an arbitrary component, as long as spinning is not adversely affected. Specific examples of such an arbitrary component include an adhesive and an electrolyte.

If the adhesive is added, nanofibers produced are adhered at contact points with each other, and therefore, upon obtaining the nanofibers in the form of a nonwoven fabric, a flexible nonwoven fabric having high tenacity and a small amount of naps caused by friction. The adhesive is not particularly limited; if the adhesive can adhere the nanofibers produced with other, and can be dissolved into a solvent of the spinning solution. Specific examples include an adhesive including a hot melt resin, an elastomer adhesive, an acrylic adhesive, an epoxy adhesive and a vinyl adhesive. Specific examples of the elastomer adhesives include a polychloroprene rubber, a styrene butadiene rubber, a butyl rubber, an acrylonitrile-butadiene rubber, an ethylene-propylene rubber, a chlorosulphonated polyethylene rubber and an epichlorhydrin rubber.

When the adhesive is added, the adhesive is preferably added in the range of approximately 0.5 to approximately 10 parts by weight based on 100 parts by weight of polypeptide in the spinning solution.

When the electrolyte is added, a charge density on a spinning solution surface can be increased, and as a result, spinnability can be improved. The electrolyte is not particularly limited, if the electrolyte can be dissolved into the spinning solution, and ionizes in the spinning solution. Specific examples include sodium chloride, calcium chloride, magnesium chloride, sodium carbonate, sodium hydrogencarbonate, sodium dihydrogen carbonate and magnesium carbonate. When the electrolyte is added, the electrolyte is desirably added approximately in an amount without causing salting out of the polypeptide in the spinning solution, and is preferably in the range of approximately 0.5 to approximately 10 parts by weight based on 100 parts by weight of the polypeptide in the spinning solution.

Subsequently, spinning is carried out according to a means of a well-known electrospinning process from the spinning solution prepared. Specifically, under a state of applying voltage between a collector (substrate) and a nozzle in which the spinning solution is filled, the spinning solution is discharged from the nozzles, and fibers are collected on the collector. Conditions for applying the electro spinning process are not particularly limited, and may be appropriately adjusted according to types of spinning solutions, an application of fibers obtained, and so forth. As general conditions in the method according to the invention, specific conditions include an applied voltage of approximately 5 to approximately 50 kV, a discharge rate of approximately 0.01 to approximately 5.00 mL/hr, and a vertical distance between the nozzle and the collector in the range of approximately 50 to approximately 300 millimeters, and a nozzle having a diameter of approximately 18 to approximately 30 G (gauge) can also be used. A spinning environment preferably includes a relative humidity of approximately 10 to approximately 70%, and a temperature of approximately 10 to approximately 30° C., but a strict control is not particularly needed.

Thus, fibers each having a diameter of approximately 5 nanometers to approximately 50 micrometers can be obtained, and nanofibers each having a diameter of approximately 5 to approximately 1,000 nanometers can also be obtained. Moreover, when spinning conditions are set and adjusted, long and unbroken fibers each having a length of approximately 200 to approximately 300 nanometers on average can be obtained. Moreover, uniform nanofibers including no clumped beads or a small amount of clumped beads, if any, can also be obtained.

(3) Measurement of Molecular Weight of Polypeptide

Here, a method for measuring the weight average molecular weight of the polypeptide according to the invention will be explained. In the invention, the weight average molecular weight of the collagen-like polypeptide single strand is measured by a gel permeation chromatography method using hexafluoroisopropanol as a solvent (hereinafter, described as an HFIP-based GPC method).

A weight average molecular weight of a high molecular weight polymer including the polypeptide has been generally measured so far according to a GPC method using an aqueous solution as a mobile phase. However, the collagen-like polypeptide single strands take the triple helical structure, and triple helices are further aggregated with each other in the aqueous solution, and thus a peak of a chromatogram has become broad, or a peak has not appeared in a position reflecting a right molecular weight of the collagen-like polypeptide single strand. For example, according to Patent literature No. 2, a molecular weight of a polypeptide is determined by a GPC method using as a column Superdex 200 HR 10/30, and using as a mobile phase a phosphoric buffer. However, replication study by the present inventors reveals that a measurement of an accurate molecular weight is quite difficult for a polypeptide having a dextran equivalent molecular weight higher than approximately 100,000. Upon studying physical properties or the like of the collagen-like polypeptide single strand obtained by the condensation reaction, a problem of difficulty in accurately measuring the molecular weight has remained even with a desire for understanding the molecular weight of the single chain.

In view of such a situation, upon producing the high molecular weight collagen-like polypeptide single strand at present, the present inventors have found that even the high molecular weight polypeptide single strand can be measured according to the HFIP-based GPC method. The fact is also based on a finding by the present inventors in which the collagen-like polypeptide single strands do not take the triple helical structure in HFIP in the range of approximately 18 to approximately 50° C. When the collagen-like polypeptide single strand is present in the form of a single molecule, an accurate molecular weight is reflected onto the peak of the chromatogram without reflecting an apparent molecular weight of a polypeptide in the triple helix or an aggregation state.

Furthermore, when PHG oligomers and a collagen-like polypeptide single strand having an absolute molecular weight determined according to a multi-angle light scattering (MALS) detector are used as molecular weight standards, the present inventors have also found that an accurate value of molecular weight of the collagen-like polypeptide single strand is obtained.

More specifically, the weight average molecular weight of the polypeptide single strand herein is measured by the HFIP-based. GPC method under conditions described below.

Mobile phase: hexafluoroisopropanol.
Column: GPC KF-606M, made by Showa Denko K. K.
Flow rate: 0.2 to 1 mL/min.
Temperature: 18 to 50° C.
Molecular weight standards: PHG oligomers and the collagen-like polypeptide single strand having the absolute molecular weight determined according to MALS.
Detection: ultraviolet spectrophotometer.

In addition, the PHG oligomers and the collagen-like polypeptide single strand as used as the molecular weight standards are represented in Table 1. Moreover, existence of the collagen-like polypeptide in the form of the single chain in the mobile phase without taking the high-order structure has been confirmed by the circular dichroism spectrum.

TABLE 1

|  | Molecular weight | Elution time (minute) |
| --- | --- | --- |
| Poly-PHG No. 1[*1] | 27,000[*3] | 4.736 |
| Poly-PHG No. 2[*1] | 11,000[*3] | 4.916 |
| $(PHG)_{10}$[*2] | 2,688[*4] | 5.213 |
| $(PHG)_{4}$[*2] | 1,086[*4] | 5.418 |
| $(PHG)_{2}$[*2] | 552[*4] | 5.652 |
| PHG[*2] | 285[*4] | 6.148 |

[*1]Produced according to the process of the invention.
[*2]Produced according to a solid-phase synthesis process.
[*3]Absolute molecular weight as determined according to MALS (DAWN HELEOS, made by Wyatt Technology Corporation).
[*4]Theoretical value of molecular weight as determined by calculation.

Moreover, if guanidine hydrochloride treatment is applied, the weight average molecular weight of the polypeptide chain according to the invention can also be measured according to the GPC method using the aqueous solution as the mobile phase. In general, a tertiary structure is not uniform in an untreated collagen-like polypeptide complex. Therefore, a plurality of peaks and a broad peak have appeared so far in measurement by GPC because, and thus measurement of an accurate molecular weight of the collagen-like peptide in the aqueous solution has been quite difficult. The present inventors have found that, when the triple helix of the collagen-like polypeptide complex is once unwound by guanidine hydrochloride, and then rewound, peaks converge into one peak even in GPC measurement using the aqueous solution as the mobile phase, and thus an accurate molecular weight can be measured.

Specifically, a collagen-like polypeptide complex is subjected to heat treatment in a guanidine hydrochloride aqueous solution, and then cooled, and a sample obtained by diluting the solution with water is used as a specimen to be provided for the GPC measurement. Here, a concentration of guanidine hydrochloride is preferably in the range of approximately 4 to approximately 6 M, further preferably, in the range of approximately 5 to approximately 6 M. The specimen is subjected to heat treatment preferably at a temperature in the range of approximately 80 to approximately 100° C. for approximately 5 to approximately 120 minutes.

The GPC measurement can be carried out under ordinary conditions, and the conditions are not particularly limited. For example, the conditions can be applied by using an aqueous solution of phosphate or the like (pH approximately 3 to approximately 6) as the mobile phase, and using as the column (TSKgel G6000PWxl, made by Tosoh Corporation) at a flow rate of approximately 0.5 to approximately 1 mL/min, and a temperature of approximately 25 to approximately 40° C., and using as the molecular weight standard Calibration Standards for Aqueous P-series/Shodex.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

Synthesis of a Collagen-Like Polypeptide Single Strand

As a PHG monomer, 0.5 g of L-propyl-L-(4-hydroxypropyl)-glycine, and 0.05 g of $HOBt.H_2O$ were weighed, and added to 5 mL of diluted solution prepared by diluting a stock PB solution, and the resultant mixture was stirred at 4° C. Then, 1.58 g of EDC.HCl was weighed in a different vessel, and in a similar manner, added to 5 mL of diluted solution prepared by diluting a stock PB solution, and the resultant mixture was stirred at 4° C. Both were mixed to start a condensation reaction, and allowed to react at 4° C. for 24 hours. Here, "stock PB solution" means an aqueous solution of 8.1 mM of $Na_2HPO_4$, 2.68 mM of KCl and 1.47 mM of $KH_2PO_4$, and reaction solvents having various phosphate ion concentrations were prepared by using the solution as a 1×PB solution. In addition, "×0" represents pure water without containing the stock PB solution.

A molecular weight (Mn and Mw) of a single chain of a product obtained was measured according to an aqueous solution-based GPC method or an HFIP-based GPC method. Measuring conditions by the aqueous solution-based GPC method include mobile phase: 20 mM of $KH_2PO_4.H_3PO_4$, pH 3.0:MeOH=8:2, column: TSK G6000 PWXL-CP, flow rate:

0.6 mL/min, temperature: 40° C. and molecular weight standards: Calibration Standards for Aqueous P-series/Shodex. Measuring conditions according to the HFIP-based GPC method include 5 mM $CF_3COONa$ HFIP solution, column: GPC KF-606M, flow rate: 0.5 mL/min, temperature: 40° C. and molecular weight standards: PHG, $(PHG)_2$, $(PHG)_4$, $(PHG)_{10}$ and a collagen-like polypeptide single strand having an absolute molecular weight determined by MALS. As a typical example, an HFIP-based GPC measurement chart of a product in Example 5 is shown in FIG. 1.

The results are represented in Table 2. In addition, Example 5 corresponds to Production Example in a phosphate ion concentration in the production method described in Patent literature No. 2. Moreover, as Reference Example, the results of $(PHG)_{10}$=2,688 g/mol were also described. Table 2 represents that a higher molecular weight polypeptide single strand was obtained as the phosphate ion concentration is smaller, and in particular, when no phosphate ion was contained (Example 1; 0 mM), the molecular weight was significantly increased. On the other hand, the molecular weight further decreased as the phosphate ion concentration was larger. Moreover, the product in Example 5 was described to have a level of several tens of thousands of molecular weight by a gel filtration method in Patent literature No. 2, but was found to have a much smaller molecular weight in measurement according to the HFIP-based GPC method.

Figure 2A:
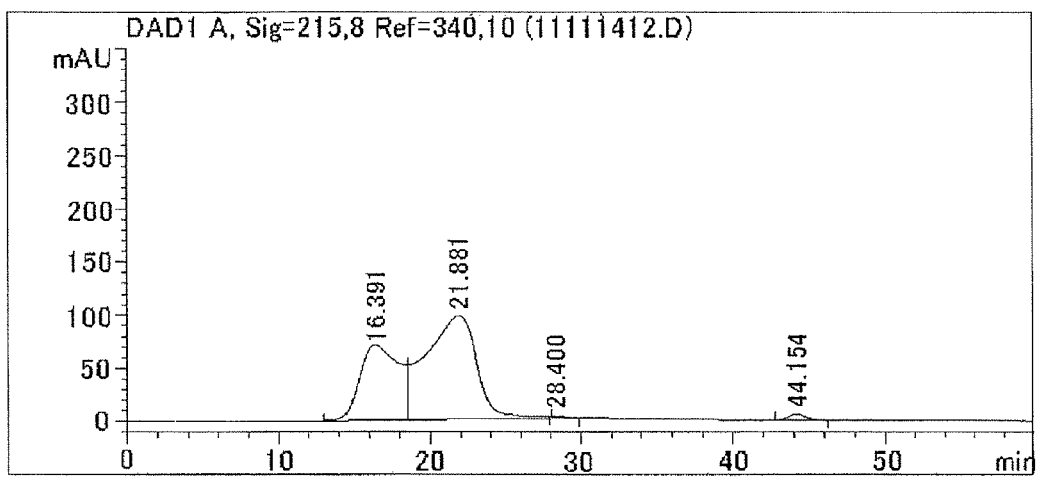
FIG. 2a and FIG. 2b show a GPC measurement chart of a collagen-like polypeptide complex (FIG. 2a: without treatment with guanidine hydrochloride, FIG. 2b: with treatment with guanidine hydrochloride).
Figure 2B:
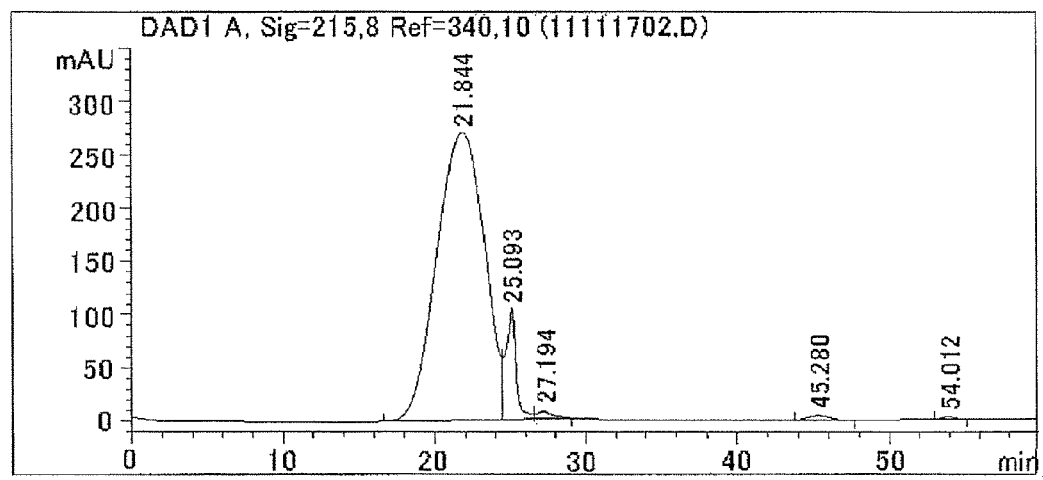

Moreover, measurement of a high molecular weight product was quite difficult according to the aqueous solution-based GPC method. However, according to the HFIP-based GPC method, the single chain of the polypeptide was allowed to make a measurement object, and an accurate measurement of the molecular weight was found to be allowed even when the measurement object was the high molecular weight polymer.

appeared broad, and understanding of a molecular weight was difficult (FIG. 2a). On the other hand, when guanidine hydrochloride treatment was applied, peaks converged into one peak, which was considered to form one tertiary structure due to rewinding of a triple helix of a collagen-like polypeptide complex (FIG. 2b). In addition, a peak appearing at 25.093 minutes in FIG. 2b originates in used guanidine hydrochloride.

Preparation of Nanofibers

The polypeptide aqueous solution after the reaction in Example 1 was freeze-dried (EYELA FDU-2000, made by Tokyo Rikakikai Co., Ltd., hereinafter, the same), and nanofibers were prepared using the same by an electrospinning process. A spinning solution was prepared by dissolving the polypeptide in hexafluoroisopropanol to be a 5 wt % solution, and a voltage of 25 kV was applied between a 27 G stainless-steel needle and a collector (vertical distance of 150 mm) by a high-voltage generator. The spinning solution was filled into a syringe connected to the needle, and extruded onto the collector at a discharge rate of 0.5 mL/hour. In addition, a relative humidity of a spinning environment was 37%, and a temperature thereof was 24° C.

Figure 3:
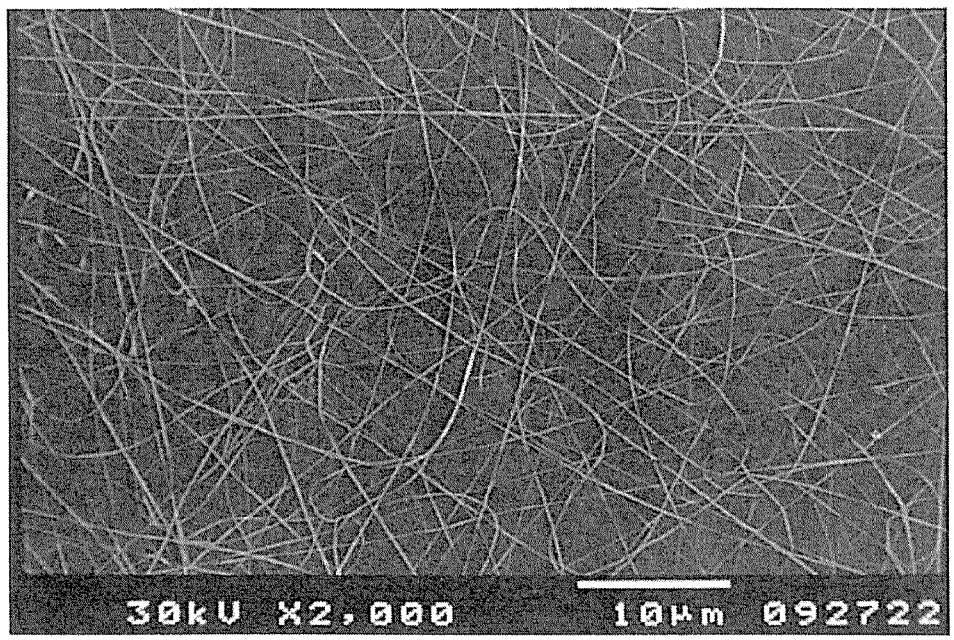
FIG. 3 shows a SEM image photograph of collagen-like polypeptide nanofibers according to the invention.
Figure 4:
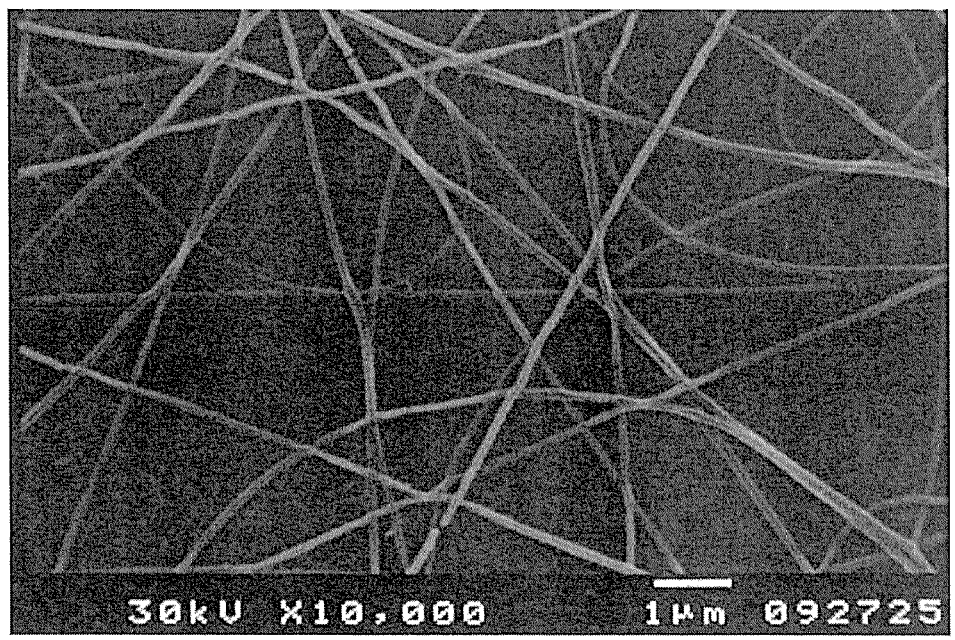
FIG. 4 shows a SEM image photograph of collagen-like polypeptide nanofibers according to the invention.

Nanofibers obtained were observed by means of a scanning electron microscope (SEM). Observation was made using a device JSM-5600 (made by JEOL Ltd.) at an accelerating voltage of 30 kV. As shown in the results in FIG. 3 and FIG. 4, the nanofibers of the collagen-like polypeptide according to the invention were in the form of uniform and long fibers each having a diameter of 100 to 200 nanometers.

In addition, a similar operation was applied using the polypeptide aqueous solution after the reaction in Example 5. However, no nanofibers were obtained without forming a fibrous form due to thread breakage or formation of beads upon spinning.

TABLE 2

| | Stock PB solution × times solution | Phosphate ion concentration | Aqueous solution-based GPC | | | HFIP-based GPC | | |
|---|---|---|---|---|---|---|---|---|
| | | | Mn | Mw | Mw/Mn | Mn | Mw | Mw/Mn |
| Example 1 | 0.00 | 0 | >200,000 | >5,000,000 | — | 14,000 | 45,600 | 1.88 |
| Example 2 | 0.25 | 2.39 | >200,000 | >5,000,000 | — | 9,800 | 26,700 | 1.68 |
| Example 3 | 0.50 | 4.79 | >200,000 | >5,000,000 | — | 8,400 | 20,300 | 1.57 |
| Example 4 | 0.75 | 7.18 | >200,000 | >5,000,000 | — | 7,200 | 16,600 | 1.52 |
| Example 5 | 1.00 | 9.57 | >200,000 | >5,000,000 | — | 7,900 | 16,000 | 1.42 |
| Example 6 | 1.25 | 11.96 | 178,000 | 2,980,000 | 16.74 | 7,200 | 13,500 | 1.37 |
| Example 7 | 1.60 | 15.31 | 237,000 | 1,380,000 | 5.82 | 6,700 | 12,000 | 1.33 |
| Example 8 | 2.70 | 25.84 | 149,000 | 353,000 | 2.36 | 5,700 | 9,600 | 1.30 |
| Example 9 | 6.00 | 57.42 | 87,300 | 125,000 | 1,43 | 4,600 | 7,100 | 1.24 |
| Reference Example | $(PHG)_{10}$ | — | — | — | — | 2,400 | 3,000 | 1.20 |

Reference: Guanidine Hydrochloride Treatment

Then, 0.5 mg/mL of polypeptide aqueous solution in Example 5 was heated at 90° C. for 1 hour in 6M guanidine hydrochloride, and then cooled to room temperature (15 to 35° C.), diluted by five times with a GPC mobile phase, and a sample obtained was provided for measurement according to an aqueous solution-based GPC method. Measuring conditions were (TSKgel G6000PWxl, made by Tosoh Corporation, a flow rate of 0.5 to 1 mL/min, a temperature of 25 to 40° C., and molecular weight standards of Calibration Standards for Aqueous P-series/Shodex).

The results are shown in FIG. 2a and FIG. 2b. In a chart when a GPC measurement was carried out without applying guanidine hydrochloride treatment, a plurality of peaks Preparation of Fibers The polypeptide aqueous solution after the reaction in Example 1 was freeze-dried, and the dried matter was dissolved into hexafluoroisopropanol to be an 8 wt % solution. The solution was filled into a syringe equipped with a 25 G syringe needle, and when the solution was extruded from the syringe needle into methanol, fibers were allowed to obtain.

In addition, with regard to the polypeptide solution after the reaction in Example 5, no thread was obtained in a similar operation.

Preparation of Gel

The polypeptide aqueous solution after the reaction in Example 1 was freeze-dried, and the dried matter was dissolved into formic acid to prepare a 1 wt % solution. Pure water was stratified onto the solution in a glass vessel, and formic acid was replaced by water, and thus a gel was obtained. The gel was formed in a bottom of the vessel, but even if the vessel was inverted and allowed to stand, the gel still formed the shape.

In addition, also with regard to the polypeptide solution after the reaction in Example 5, a gel was obtained in a similar operation. However, the gel was softer than the gel prepared using the solution in Example 1, and had strength at an almost collapsible level by inversion of the vessel.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

Industrial Applicability

According to the invention, a molecular weight of a collagen-like polypeptide single strand to be formed can be controlled in desired magnitude by a simple and inexpensive means, and ever-larger molecular weight collagen-like polypeptide single strand can be produced. When a collagen-like polypeptide single strand having various molecular weights, in particular, a high molecular weight collagen-like polypeptide single strand and a complex thereof can be obtained, processability thereof is significantly improved, and a width of application as a functional material is extended, and therefore the collagen is industrially very useful.

What is claimed is:

1. A method for producing a polypeptide, comprising a step for allowing peptide oligomers represented by any one of formulas (1) to (3) (SEQ ID No:1 to SEQ ID No:3) below to polymerize by a condensation reaction, wherein the condensation reaction is carried out in an aqueous solvent containing a phosphate ion in the range of 0 M to 0.0025 M in the presence of a condensation agent, or a condensation agent and a condensation auxiliary:

H-(Pro-Y-Gly)$_n$-OH　　(1)(SEQ ID No:1);

H-(Y-Gly-Pro)$_n$-OH　　(2)(SEQ ID No:2); and

H-(Gly-Pro-Y)$_n$-OH　　(3)(SEQ ID No:3);

wherein, in formulas (1) to (3) (SEQ ID No:1 to SEQ ID No:3), Y is hydroxyproline or proline, and n is an integer from 1 to 10.

2. A method for controlling a molecular weight of a product to be obtained by a condensation reaction of peptide oligomers represented by any one of formulas (1) to (3) (SEQ ID No:1 to SEQ ID No:3) below in an aqueous solvent containing a phosphate ion, wherein a concentration of the phosphate ion is adjusted in the range of 0 to 0.0025 M in the condensation reaction:

H-(Pro-Y-Gly)$_n$-OH　　(1)(SEQ ID No:1);

H-(Y-Gly-Pro)$_n$-OH　　(2)(SEQ ID No:2); and

H-(Gly-Pro-Y)$_n$-OH　　(3)(SEQ ID No:3);

wherein, in formulas (1) to (3) (SEQ ID No:1 to SEQ ID No:3), Y is hydroxyproline or proline, and n is an integer from 1 to 10.

3. A polypeptide having a peptide fragment represented by formula (4) (SEQ ID No:4) below:

-(Pro-Y-Gly)$_m$-　　(4)(SEQ ID No:4)

wherein, in formula (4) (SEQ ID No:4), Y is hydroxyproline or proline, and m is an integer from 100 to 171, wherein a weight average molecular weight of a single chain measured by an HFIP-based GPC method is in the range of 26,700 to 45,600.

4. A nanofiber comprising the polypeptide according to claim 3.

* * * * *

```
                        SEQUENCE LISTING

<160> NUMBER OF SEQ ID NOS: 68

<210> SEQ ID NO 1
<211> LENGTH: 30
<212> TYPE: PRT
<213> ORGANISM: Artificial
<220> FEATURE:
<223> OTHER INFORMATION: seq.1
<220> FEATURE:
<221> NAME/KEY: MISC_FEATURE
<222> LOCATION: (1)..(30)
<223> OTHER INFORMATION: A synthesized peptide oligomer for producing a
      collagen-like polypeptide, wherein X presents Pro or Hyp. "PXG"
      can repeat 1 to 10 times, and the length can vary from 3 to 30.

<400> SEQUENCE: 1

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly
            20                  25                  30

<210> SEQ ID NO 2
<211> LENGTH: 30
<212> TYPE: PRT
<213> ORGANISM: Artificial
<220> FEATURE:
<223> OTHER INFORMATION: seq.2
<220> FEATURE:
<221> NAME/KEY: MISC_FEATURE
<222> LOCATION: (1)..(30)
<223> OTHER INFORMATION: A synthesized peptide oligomer for producing a
      collagen-like polypeptide, wherein X presents Pro or Hyp. "XGP"
      can repeat 1 to 10 times, and the length can vary from 3 to 30.

<400> SEQUENCE: 2

Xaa Gly Pro Xaa Gly Pro Xaa Gly Pro Xaa Gly Pro Xaa Gly Pro Xaa
1               5                   10                  15

Gly Pro Xaa Gly Pro Xaa Gly Pro Xaa Gly Pro Xaa Gly Pro
            20                  25                  30

<210> SEQ ID NO 3
<211> LENGTH: 30
<212> TYPE: PRT
<213> ORGANISM: Artificial
<220> FEATURE:
<223> OTHER INFORMATION: seq.3
<220> FEATURE:
<221> NAME/KEY: MISC_FEATURE
<222> LOCATION: (1)..(30)
<223> OTHER INFORMATION: A synthesized peptide oligomer for producing a
      collagen-like polypeptide, wherein X presents Pro or Hyp. "GPX"
      can repeat 1 to 10 times, and the length can vary from 3 to 30.
```

```
<400> SEQUENCE: 3

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa
            20                  25                  30

<210> SEQ ID NO 4
<211> LENGTH: 513
<212> TYPE: PRT
<213> ORGANISM: Artificial
<220> FEATURE:
<223> OTHER INFORMATION: seq.4
<220> FEATURE:
<221> NAME/KEY: MISC_FEATURE
<222> LOCATION: (1)..(513)
<223> OTHER INFORMATION: A synthesized peptide oligomer for producing
      a collagen-like polypeptide, wherein X presents Pro or Hyp. "PXG"
      can repeat 100 to 171 times, and the length can vary from 3 00
      to 513.

<400> SEQUENCE: 4

Pro Xaa Gly Pro Xaa Gly Pro Xaa Gly Pro Xaa Gly Pro Xaa Gly Pro
1               5                   10                  15

Xaa Gly Pro Xaa Gly Pro Xaa Gly Pro Xaa Gly Pro Xaa Gly Pro Xaa
            20                  25                  30

Gly Pro Xaa Gly Pro Xaa Gly Pro Xaa Gly Pro Xaa Gly Pro Xaa Gly
        35                  40                  45

Pro Xaa Gly Pro Xaa Gly Pro Xaa Gly Pro Xaa Gly Pro Xaa Gly Pro
    50                  55                  60

Xaa Gly Pro Xaa Gly Pro Xaa Gly Pro Xaa Gly Pro Xaa Gly Pro Xaa
65              70                  75                  80

Gly Pro Xaa Gly Pro Xaa Gly Pro Xaa Gly Pro Xaa Gly Pro Xaa Gly
            85                  90                  95

Pro Xaa Gly Pro Xaa Gly Pro Xaa Gly Pro Xaa Gly Pro Xaa Gly Pro
        100                 105                 110

Xaa Gly Pro Xaa Gly Pro Xaa Gly Pro Xaa Gly Pro Xaa Gly Pro Xaa
    115                 120                 125

Gly Pro Xaa Gly Pro Xaa Gly Pro Xaa Gly Pro Xaa Gly Pro Xaa Gly
    130                 135                 140

Pro Xaa Gly Pro Xaa Gly Pro Xaa Gly Pro Xaa Gly Pro Xaa Gly Pro
145                 150                 155                 160

Xaa Gly Pro Xaa Gly Pro Xaa Gly Pro Xaa Gly Pro Xaa Gly Pro Xaa
            165                 170                 175

Gly Pro Xaa Gly Pro Xaa Gly Pro Xaa Gly Pro Xaa Gly Pro Xaa Gly
        180                 185                 190

Pro Xaa Gly Pro Xaa Gly Pro Xaa Gly Pro Xaa Gly Pro Xaa Gly Pro
    195                 200                 205

Xaa Gly Pro Xaa Gly Pro Xaa Gly Pro Xaa Gly Pro Xaa Gly Pro Xaa
    210                 215                 220

Gly Pro Xaa Gly Pro Xaa Gly Pro Xaa Gly Pro Xaa Gly Pro Xaa Gly
225                 230                 235                 240

Pro Xaa Gly Pro Xaa Gly Pro Xaa Gly Pro Xaa Gly Pro Xaa Gly Pro
            245                 250                 255

Xaa Gly Pro Xaa Gly Pro Xaa Gly Pro Xaa Gly Pro Xaa Gly Pro Xaa
        260                 265                 270

Gly Pro Xaa Gly Pro Xaa Gly Pro Xaa Gly Pro Xaa Gly Pro Xaa Gly
    275                 280                 285
```

Pro Xaa Gly Pro Xaa Gly Pro Xaa Gly Pro Xaa Gly Pro
        290                 295                 300

Xaa Gly Pro Xaa Gly Pro Xaa Gly Pro Xaa Gly Pro Xaa
305                 310                 315                 320

Gly Pro Xaa Gly Pro Xaa Gly Pro Xaa Gly Pro Xaa Gly
                325                 330                 335

Pro Xaa Gly Pro Xaa Gly Pro Xaa Gly Pro Xaa Gly Pro
        340                 345                 350

Xaa Gly Pro Xaa Gly Pro Xaa Gly Pro Xaa Gly Pro Xaa
            355                 360                 365

Gly Pro Xaa Gly Pro Xaa Gly Pro Xaa Gly Pro Xaa Gly
    370                 375                 380

Pro Xaa Gly Pro Xaa Gly Pro Xaa Gly Pro Xaa Gly Pro
385                 390                 395                 400

Xaa Gly Pro Xaa Gly Pro Xaa Gly Pro Xaa Gly Pro Xaa
                405                 410                 415

Gly Pro Xaa Gly Pro Xaa Gly Pro Xaa Gly Pro Xaa Gly
        420                 425                 430

Pro Xaa Gly Pro Xaa Gly Pro Xaa Gly Pro Xaa Gly Pro
            435                 440                 445

Xaa Gly Pro Xaa Gly Pro Xaa Gly Pro Xaa Gly Pro Xaa
    450                 455                 460

Gly Pro Xaa Gly Pro Xaa Gly Pro Xaa Gly Pro Xaa Gly
465                 470                 475                 480

Pro Xaa Gly Pro Xaa Gly Pro Xaa Gly Pro Xaa Gly Pro
                485                 490                 495

Xaa Gly Pro Xaa Gly Pro Xaa Gly Pro Xaa Gly Pro Xaa
        500                 505                 510

Gly

<210> SEQ ID NO 5
<211> LENGTH: 30
<212> TYPE: PRT
<213> ORGANISM: Artificial
<220> FEATURE:
<223> OTHER INFORMATION: seq.5
<220> FEATURE:
<221> NAME/KEY: MISC_FEATURE
<222> LOCATION: (1)..(30)
<223> OTHER INFORMATION: A synthesized peptide oligomer for producing
    a collagen-like polypeptide, wherein "DPG" can repeat 1 to 10
    times, and the length can vary from 3 to 30.

<400> SEQUENCE: 5

Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly
            20                  25                  30

<210> SEQ ID NO 6
<211> LENGTH: 30
<212> TYPE: PRT
<213> ORGANISM: Artificial
<220> FEATURE:
<223> OTHER INFORMATION: seq.6
<220> FEATURE:
<221> NAME/KEY: MISC_FEATURE
<222> LOCATION: (1)..(30)
<223> OTHER INFORMATION: A synthesized peptide oligomer for producing a
    collagen-like polypeptide, wherein X presents Hyp. "DXG" can
    repeat 1 to 10 times, and the length can vary from 3 to 30.

```
<400> SEQUENCE: 6

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly
            20                  25                  30

<210> SEQ ID NO 7
<211> LENGTH: 30
<212> TYPE: PRT
<213> ORGANISM: Artificial
<220> FEATURE:
<223> OTHER INFORMATION: seq.7
<220> FEATURE:
<221> NAME/KEY: MISC_FEATURE
<222> LOCATION: (1)..(30)
<223> OTHER INFORMATION: A synthesized peptide oligomer for producing
      a collagen-like polypeptide, wherein "EPG" can repeat 1 to 10
      times, and the length can vary from 3 to 30.

<400> SEQUENCE: 7

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly
            20                  25                  30

<210> SEQ ID NO 8
<211> LENGTH: 30
<212> TYPE: PRT
<213> ORGANISM: Artificial
<220> FEATURE:
<223> OTHER INFORMATION: seq.8
<220> FEATURE:
<221> NAME/KEY: MISC_FEATURE
<222> LOCATION: (1)..(30)
<223> OTHER INFORMATION: A synthesized peptide oligomer for producing
      a collagen-like polypeptide, wherein X presents Hyp. "EXG" can
      repeat 1 to 10 times, and the length can vary from 3 to 30.

<400> SEQUENCE: 8

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly
            20                  25                  30

<210> SEQ ID NO 9
<211> LENGTH: 60
<212> TYPE: PRT
<213> ORGANISM: Artificial
<220> FEATURE:
<223> OTHER INFORMATION: seq.9
<220> FEATURE:
<221> NAME/KEY: MISC_FEATURE
<222> LOCATION: (1)..(60)
<223> OTHER INFORMATION: A synthesized peptide oligomer for producing
      a collagen-like polypeptide, wherein "PQGIAG" can repeat 1 to 10
      times, and the length can vary from 6 to 60.

<400> SEQUENCE: 9

Pro Gln Gly Ile Ala Gly Pro Gln Gly Ile Ala Gly Pro Gln Gly Ile
1               5                   10                  15

Ala Gly Pro Gln Gly Ile Ala Gly Pro Gln Gly Ile Ala Gly Pro Gln
            20                  25                  30

Gly Ile Ala Gly Pro Gln Gly Ile Ala Gly Pro Gln Gly Ile Ala Gly
        35                  40                  45

Pro Gln Gly Ile Ala Gly Pro Gln Gly Ile Ala Gly
    50                  55                  60
```

<210> SEQ ID NO 10
<211> LENGTH: 60
<212> TYPE: PRT
<213> ORGANISM: Artificial
<220> FEATURE:
<223> OTHER INFORMATION: seq.10
<220> FEATURE:
<221> NAME/KEY: MISC_FEATURE
<223> OTHER INFORMATION: A synthesized peptide oligomer for producing a
      collagen-like polypeptide, wherein "PNGIAG" can repeat 1 to 10
      times, and the length can vary from 6 to 60.
<220> FEATURE:
<221> NAME/KEY: MISC_FEATURE
<222> LOCATION: (1)..(60)
<223> OTHER INFORMATION: "PNGIAG" can repeat 1 to 10 times, and the
      length can vary from 6 to 60.

<400> SEQUENCE: 10

Pro Asn Gly Ile Ala Gly Pro Asn Gly Ile Ala Gly Pro Asn Gly Ile
1               5                   10                  15

Ala Gly Pro Asn Gly Ile Ala Gly Pro Asn Gly Ile Ala Gly Pro Asn
            20                  25                  30

Gly Ile Ala Gly Pro Asn Gly Ile Ala Gly Pro Asn Gly Ile Ala Gly
        35                  40                  45

Pro Asn Gly Ile Ala Gly Pro Asn Gly Ile Ala Gly
    50                  55                  60

<210> SEQ ID NO 11
<211> LENGTH: 60
<212> TYPE: PRT
<213> ORGANISM: Artificial
<220> FEATURE:
<223> OTHER INFORMATION: seq.11
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PLGIAG" can repeat 1 to 10
      times, and the length can vary from 6 to 60.

<400> SEQUENCE: 11

Pro Leu Gly Ile Ala Gly Pro Leu Gly Ile Ala Gly Pro Leu Gly Ile
1               5                   10                  15

Ala Gly Pro Leu Gly Ile Ala Gly Pro Leu Gly Ile Ala Gly Pro Leu
            20                  25                  30

Gly Ile Ala Gly Pro Leu Gly Ile Ala Gly Pro Leu Gly Ile Ala Gly
        35                  40                  45

Pro Leu Gly Ile Ala Gly Pro Leu Gly Ile Ala Gly
    50                  55                  60

<210> SEQ ID NO 12
<211> LENGTH: 60
<212> TYPE: PRT
<213> ORGANISM: Artificial
<220> FEATURE:
<223> OTHER INFORMATION: seq.12
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PIGIAG" can repeat 1 to 10
      times, and the length can vary from 6 to 60.

<400> SEQUENCE: 12

Pro Ile Gly Ile Ala Gly Pro Ile Gly Ile Ala Gly Pro Ile Gly Ile
1               5                   10                  15

```
Ala Gly Pro Ile Gly Ile Ala Gly Pro Ile Gly Ile Ala Gly Pro Ile
            20                  25                  30

Gly Ile Ala Gly Pro Ile Gly Ile Ala Gly Pro Ile Gly Ile Ala Gly
        35                  40                  45

Pro Ile Gly Ile Ala Gly Pro Ile Gly Ile Ala Gly
    50                  55                  60

<210> SEQ ID NO 13
<211> LENGTH: 60
<212> TYPE: PRT
<213> ORGANISM: Artificial
<220> FEATURE:
<223> OTHER INFORMATION: seq.13
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PVGIAG" can repeat 1 to 10
      times, and the length can vary from 6 to 60.

<400> SEQUENCE: 13

Pro Val Gly Ile Ala Gly Pro Val Gly Ile Ala Gly Pro Val Gly Ile
1               5                   10                  15

Ala Gly Pro Val Gly Ile Ala Gly Pro Val Gly Ile Ala Gly Pro Val
            20                  25                  30

Gly Ile Ala Gly Pro Val Gly Ile Ala Gly Pro Val Gly Ile Ala Gly
        35                  40                  45

Pro Val Gly Ile Ala Gly Pro Val Gly Ile Ala Gly
    50                  55                  60

<210> SEQ ID NO 14
<211> LENGTH: 60
<212> TYPE: PRT
<213> ORGANISM: Artificial
<220> FEATURE:
<223> OTHER INFORMATION: seq.14
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PAGIAG" can repeat 1 to 10
      times, and the length can vary from 6 to 60.

<400> SEQUENCE: 14

Pro Ala Gly Ile Ala Gly Pro Ala Gly Ile Ala Gly Pro Ala Gly Ile
1               5                   10                  15

Ala Gly Pro Ala Gly Ile Ala Gly Pro Ala Gly Ile Ala Gly Pro Ala
            20                  25                  30

Gly Ile Ala Gly Pro Ala Gly Ile Ala Gly Pro Ala Gly Ile Ala Gly
        35                  40                  45

Pro Ala Gly Ile Ala Gly Pro Ala Gly Ile Ala Gly
    50                  55                  60

<210> SEQ ID NO 15
<211> LENGTH: 60
<212> TYPE: PRT
<213> ORGANISM: Artificial
<220> FEATURE:
<223> OTHER INFORMATION: seq.15
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PQGLAG" can repeat 1 to 10
      times, and the length can vary from 6 to 60.
```

<400> SEQUENCE: 15

Pro Gln Gly Leu Ala Gly Pro Gln Gly Leu Ala Gly Pro Gln Gly Leu
1               5                   10                  15

Ala Gly Pro Gln Gly Leu Ala Gly Pro Gln Gly Leu Ala Gly Pro Gln
            20                  25                  30

Gly Leu Ala Gly Pro Gln Gly Leu Ala Gly Pro Gln Gly Leu Ala Gly
        35                  40                  45

Pro Gln Gly Leu Ala Gly Pro Gln Gly Leu Ala Gly
    50                  55                  60

<210> SEQ ID NO 16
<211> LENGTH: 60
<212> TYPE: PRT
<213> ORGANISM: Artificial
<220> FEATURE:
<223> OTHER INFORMATION: seq.16
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PNGLAG" can repeat 1 to 10
      times, and the length can vary from 6 to 60.

<400> SEQUENCE: 16

Pro Asn Gly Leu Ala Gly Pro Asn Gly Leu Ala Gly Pro Asn Gly Leu
1               5                   10                  15

Ala Gly Pro Asn Gly Leu Ala Gly Pro Asn Gly Leu Ala Gly Pro Asn
            20                  25                  30

Gly Leu Ala Gly Pro Asn Gly Leu Ala Gly Pro Asn Gly Leu Ala Gly
        35                  40                  45

Pro Asn Gly Leu Ala Gly Pro Asn Gly Leu Ala Gly
    50                  55                  60

<210> SEQ ID NO 17
<211> LENGTH: 60
<212> TYPE: PRT
<213> ORGANISM: Artificial
<220> FEATURE:
<223> OTHER INFORMATION: seq.17
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PLGLAG" can repeat 1 to 10
      times, and the length can vary from 6 to 60.

<400> SEQUENCE: 17

Pro Leu Gly Leu Ala Gly Pro Leu Gly Leu Ala Gly Pro Leu Gly Leu
1               5                   10                  15

Ala Gly Pro Leu Gly Leu Ala Gly Pro Leu Gly Leu Ala Gly Pro Leu
            20                  25                  30

Gly Leu Ala Gly Pro Leu Gly Leu Ala Gly Pro Leu Gly Leu Ala Gly
        35                  40                  45

Pro Leu Gly Leu Ala Gly Pro Leu Gly Leu Ala Gly
    50                  55                  60

<210> SEQ ID NO 18
<211> LENGTH: 60
<212> TYPE: PRT
<213> ORGANISM: Artificial
<220> FEATURE:
<223> OTHER INFORMATION: seq.18
<220> FEATURE:

```
<221> NAME/KEY: MISC_FEATURE
<222> LOCATION: (1)..(60)
<223> OTHER INFORMATION: A synthesized peptide oligomer for producing a
      collagen-like polypeptide, wherein "PIGLAG" can repeat 1 to 10
      times, and the length can vary from 6 to 60.

<400> SEQUENCE: 18

Pro Ile Gly Leu Ala Gly Pro Ile Gly Leu Ala Gly Pro Ile Gly Leu
1               5                   10                  15

Ala Gly Pro Ile Gly Leu Ala Gly Pro Ile Gly Leu Ala Gly Pro Ile
            20                  25                  30

Gly Leu Ala Gly Pro Ile Gly Leu Ala Gly Pro Ile Gly Leu Ala Gly
        35                  40                  45

Pro Ile Gly Leu Ala Gly Pro Ile Gly Leu Ala Gly
        50                  55                  60

<210> SEQ ID NO 19
<211> LENGTH: 60
<212> TYPE: PRT
<213> ORGANISM: Artificial
<220> FEATURE:
<223> OTHER INFORMATION: seq.19
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PVGLAG" can repeat 1 to 10
      times, and the length can vary from 6 to 60.

<400> SEQUENCE: 19

Pro Val Gly Leu Ala Gly Pro Val Gly Leu Ala Gly Pro Val Gly Leu
1               5                   10                  15

Ala Gly Pro Val Gly Leu Ala Gly Pro Val Gly Leu Ala Gly Pro Val
            20                  25                  30

Gly Leu Ala Gly Pro Val Gly Leu Ala Gly Pro Val Gly Leu Ala Gly
        35                  40                  45

Pro Val Gly Leu Ala Gly Pro Val Gly Leu Ala Gly
        50                  55                  60

<210> SEQ ID NO 20
<211> LENGTH: 60
<212> TYPE: PRT
<213> ORGANISM: Artificial
<220> FEATURE:
<223> OTHER INFORMATION: seq.20
<220> FEATURE:
<221> NAME/KEY: MISC_FEATURE
<222> LOCATION: (1)..(60)
<223> OTHER INFORMATION: A synthesized peptide oligomer for producing a
      collagen-like polypeptide, wherein "PAGLAG" can repeat 1 to 10
      times, and the length can vary from 6 to 60.

<400> SEQUENCE: 20

Pro Ala Gly Leu Ala Gly Pro Ala Gly Leu Ala Gly Pro Ala Gly Leu
1               5                   10                  15

Ala Gly Pro Ala Gly Leu Ala Gly Pro Ala Gly Leu Ala Gly Pro Ala
            20                  25                  30

Gly Leu Ala Gly Pro Ala Gly Leu Ala Gly Pro Ala Gly Leu Ala Gly
        35                  40                  45

Pro Ala Gly Leu Ala Gly Pro Ala Gly Leu Ala Gly
        50                  55                  60

<210> SEQ ID NO 21
<211> LENGTH: 90
```

```
<212> TYPE: PRT
<213> ORGANISM: Artificial
<220> FEATURE:
<223> OTHER INFORMATION: seq.21
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PQGIAG"can repeat 1
      to 10 times, respectively, and the length can vary from 9 to 90.

<400> SEQUENCE: 21

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Gln
            20                  25                  30

Gly Ile Ala Gly Pro Gln Gly Ile Ala Gly Pro Gln Gly Ile Ala Gly
        35                  40                  45

Pro Gln Gly Ile Ala Gly Pro Gln Gly Ile Ala Gly Pro Gln Gly Ile
    50                  55                  60

Ala Gly Pro Gln Gly Ile Ala Gly Pro Gln Gly Ile Ala Gly Pro Gln
65                  70                  75                  80

Gly Ile Ala Gly Pro Gln Gly Ile Ala Gly
            85                  90

<210> SEQ ID NO 22
<211> LENGTH: 90
<212> TYPE: PRT
<213> ORGANISM: Artificial
<220> FEATURE:
<223> OTHER INFORMATION: seq.22
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PNGIAG"can repeat 1
      to 10 times, respectively, and the length can vary from 9 to 90.

<400> SEQUENCE: 22

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Asn
            20                  25                  30

Gly Ile Ala Gly Pro Asn Gly Ile Ala Gly Pro Asn Gly Ile Ala Gly
        35                  40                  45

Pro Asn Gly Ile Ala Gly Pro Asn Gly Ile Ala Gly Pro Asn Gly Ile
    50                  55                  60

Ala Gly Pro Asn Gly Ile Ala Gly Pro Asn Gly Ile Ala Gly Pro Asn
65                  70                  75                  80

Gly Ile Ala Gly Pro Asn Gly Ile Ala Gly
            85                  90

<210> SEQ ID NO 23
<211> LENGTH: 90
<212> TYPE: PRT
<213> ORGANISM: Artificial
<220> FEATURE:
<223> OTHER INFORMATION: seq.23
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PLGIAG"can repeat 1
      to 10 times, respectively, and the length can vary from 9 to 90.
```

35

-continued

```
<400> SEQUENCE: 23

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Leu
            20                  25                  30

Gly Ile Ala Gly Pro Leu Gly Ile Ala Gly Pro Leu Gly Ile Ala Gly
        35                  40                  45

Pro Leu Gly Ile Ala Gly Pro Leu Gly Ile Ala Gly Pro Leu Gly Ile
    50                  55                  60

Ala Gly Pro Leu Gly Ile Ala Gly Pro Leu Gly Ile Ala Gly Pro Leu
65                  70                  75                  80

Gly Ile Ala Gly Pro Leu Gly Ile Ala Gly
                85                  90

<210> SEQ ID NO 24
<211> LENGTH: 90
<212> TYPE: PRT
<213> ORGANISM: Artificial
<220> FEATURE:
<223> OTHER INFORMATION: seq.24
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PIGIAG"can repeat 1
      to 10 times, respectively, and the length can vary from 9 to 90.

<400> SEQUENCE: 24

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Ile
            20                  25                  30

Gly Ile Ala Gly Pro Ile Gly Ile Ala Gly Pro Ile Gly Ile Ala Gly
        35                  40                  45

Pro Ile Gly Ile Ala Gly Pro Ile Gly Ile Ala Gly Pro Ile Gly Ile
    50                  55                  60

Ala Gly Pro Ile Gly Ile Ala Gly Pro Ile Gly Ile Ala Gly Pro Ile
65                  70                  75                  80

Gly Ile Ala Gly Pro Ile Gly Ile Ala Gly
                85                  90

<210> SEQ ID NO 25
<211> LENGTH: 90
<212> TYPE: PRT
<213> ORGANISM: Artificial
<220> FEATURE:
<223> OTHER INFORMATION: seq.25
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PVGIAG"can repeat 1
      to 10 times, respectively, and the length can vary from 9 to 90.

<400> SEQUENCE: 25

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Val
            20                  25                  30

Gly Ile Ala Gly Pro Val Gly Ile Ala Gly Pro Val Gly Ile Ala Gly
        35                  40                  45
```

```
Pro Val Gly Ile Ala Gly Pro Val Gly Ile Ala Gly Pro Val Gly Ile
        50                  55                  60

Ala Gly Pro Val Gly Ile Ala Gly Pro Val Gly Ile Ala Gly Pro Val
65                  70                  75                  80

Gly Ile Ala Gly Pro Val Gly Ile Ala Gly
                85                  90

<210> SEQ ID NO 26
<211> LENGTH: 90
<212> TYPE: PRT
<213> ORGANISM: Artificial
<220> FEATURE:
<223> OTHER INFORMATION: seq.26
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PAGIAG"can repeat 1
      to 10 times, respectively, and the length can vary from 9 to 90.

<400> SEQUENCE: 26

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Ala
                20                  25                  30

Gly Ile Ala Gly Pro Ala Gly Ile Ala Gly Pro Ala Gly Ile Ala Gly
            35                  40                  45

Pro Ala Gly Ile Ala Gly Pro Ala Gly Ile Ala Gly Pro Ala Gly Ile
        50                  55                  60

Ala Gly Pro Ala Gly Ile Ala Gly Pro Ala Gly Ile Ala Gly Pro Ala
65                  70                  75                  80

Gly Ile Ala Gly Pro Ala Gly Ile Ala Gly
                85                  90

<210> SEQ ID NO 27
<211> LENGTH: 90
<212> TYPE: PRT
<213> ORGANISM: Artificial
<220> FEATURE:
<223> OTHER INFORMATION: seq.27
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PQGLAG"can repeat 1
      to 10 times, respectively, and the length can vary from 9 to 90.

<400> SEQUENCE: 27

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Gln
                20                  25                  30

Gly Leu Ala Gly Pro Gln Gly Leu Ala Gly Pro Gln Gly Leu Ala Gly
            35                  40                  45

Pro Gln Gly Leu Ala Gly Pro Gln Gly Leu Ala Gly Pro Gln Gly Leu
        50                  55                  60

Ala Gly Pro Gln Gly Leu Ala Gly Pro Gln Gly Leu Ala Gly Pro Gln
65                  70                  75                  80

Gly Leu Ala Gly Pro Gln Gly Leu Ala Gly
                85                  90

<210> SEQ ID NO 28
```

```
<211> LENGTH: 90
<212> TYPE: PRT
<213> ORGANISM: Artificial
<220> FEATURE:
<223> OTHER INFORMATION: seq.28
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PNGLAG"can repeat 1
      to 10 times, respectively, and the length can vary from 9 to 90.

<400> SEQUENCE: 28

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Asn
                20                  25                  30

Gly Leu Ala Gly Pro Asn Gly Leu Ala Gly Pro Asn Gly Leu Ala Gly
            35                  40                  45

Pro Asn Gly Leu Ala Gly Pro Asn Gly Leu Ala Gly Pro Asn Gly Leu
    50                  55                  60

Ala Gly Pro Asn Gly Leu Ala Gly Pro Asn Gly Leu Ala Gly Pro Asn
65                  70                  75                  80

Gly Leu Ala Gly Pro Asn Gly Leu Ala Gly
                85                  90

<210> SEQ ID NO 29
<211> LENGTH: 90
<212> TYPE: PRT
<213> ORGANISM: Artificial
<220> FEATURE:
<223> OTHER INFORMATION: seq.29
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PLGLAG"can repeat 1
      to 10 times, respectively, and the length can vary from 9 to 90.

<400> SEQUENCE: 29

Asp Pro Gly Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Leu
                20                  25                  30

Gly Leu Ala Gly Pro Leu Gly Leu Ala Gly Pro Leu Gly Leu Ala Gly
            35                  40                  45

Pro Leu Gly Leu Ala Gly Pro Leu Gly Leu Ala Gly Pro Leu Gly Leu
    50                  55                  60

Ala Gly Pro Leu Gly Leu Ala Gly Pro Leu Gly Leu Ala Gly Pro Leu
65                  70                  75                  80

Gly Leu Ala Gly Pro Leu Gly Leu Ala Gly
                85                  90

<210> SEQ ID NO 30
<211> LENGTH: 90
<212> TYPE: PRT
<213> ORGANISM: Artificial
<220> FEATURE:
<223> OTHER INFORMATION: seq.30
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PIGLAG"can repeat 1
      to 10 times, respectively, and the length can vary from 9 to 90.
```

<400> SEQUENCE: 30

Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Ile
            20                  25                  30

Gly Leu Ala Gly Pro Ile Gly Leu Ala Gly Pro Ile Gly Leu Ala Gly
        35                  40                  45

Pro Ile Gly Leu Ala Gly Pro Ile Gly Leu Ala Gly Pro Ile Gly Leu
    50                  55                  60

Ala Gly Pro Ile Gly Leu Ala Gly Pro Ile Gly Leu Ala Gly Pro Ile
65                  70                  75                  80

Gly Leu Ala Gly Pro Ile Gly Leu Ala Gly
            85                  90

<210> SEQ ID NO 31
<211> LENGTH: 90
<212> TYPE: PRT
<213> ORGANISM: Artificial
<220> FEATURE:
<223> OTHER INFORMATION: seq.31
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PVGLAG"can repeat 1
      to 10 times, respectively, and the length can vary from 9 to 90.

<400> SEQUENCE: 31

Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Val
            20                  25                  30

Gly Leu Ala Gly Pro Val Gly Leu Ala Gly Pro Val Gly Leu Ala Gly
        35                  40                  45

Pro Val Gly Leu Ala Gly Pro Val Gly Leu Ala Gly Pro Val Gly Leu
    50                  55                  60

Ala Gly Pro Val Gly Leu Ala Gly Pro Val Gly Leu Ala Gly Pro Val
65                  70                  75                  80

Gly Leu Ala Gly Pro Val Gly Leu Ala Gly
            85                  90

<210> SEQ ID NO 32
<211> LENGTH: 90
<212> TYPE: PRT
<213> ORGANISM: Artificial
<220> FEATURE:
<223> OTHER INFORMATION: seq.32
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "DPG" and "PAGLAG"can repeat 1
      to 10 times, respectively, and the length can vary from 9 to 90.

<400> SEQUENCE: 32

Asp Pro Gly Asp Pro Gly Asp Pro Gly Asp Pro Gly Asp
1               5                   10                  15

Pro Gly Asp Pro Gly Asp Pro Gly Asp Pro Gly Asp Pro Gly Pro Ala
            20                  25                  30

Gly Leu Ala Gly Pro Ala Gly Leu Ala Gly Pro Ala Gly Leu Ala Gly
        35                  40                  45

```
Pro Ala Gly Leu Ala Gly Pro Ala Gly Leu Ala Gly Pro Ala Gly Leu
         50                   55                   60

Ala Gly Pro Ala Gly Leu Ala Gly Pro Ala Gly Leu Ala Gly Pro Ala
 65                  70                   75                   80

Gly Leu Ala Gly Pro Ala Gly Leu Ala Gly
                 85                   90

<210> SEQ ID NO 33
<211> LENGTH: 90
<212> TYPE: PRT
<213> ORGANISM: Artificial
<220> FEATURE:
<223> OTHER INFORMATION: seq.33
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PQGIAG"can repeat 1 to 10 times, respectively, and the length
      can vary from 9 to 90.

<400> SEQUENCE: 33

Asp Xaa Gly Asp Xaa Gly Asp Xaa Gly Asp Xaa Gly Asp Xaa Gly Asp
 1               5                   10                  15

Xaa Gly Asp Xaa Gly Asp Xaa Gly Asp Xaa Gly Asp Xaa Gly Pro Gln
                20                  25                  30

Gly Ile Ala Gly Pro Gln Gly Ile Ala Gly Pro Gln Gly Ile Ala Gly
         35                  40                  45

Pro Gln Gly Ile Ala Gly Pro Gln Gly Ile Ala Gly Pro Gln Gly Ile
 50                  55                  60

Ala Gly Pro Gln Gly Ile Ala Gly Pro Gln Gly Ile Ala Gly Pro Gln
 65                  70                  75                  80

Gly Ile Ala Gly Pro Gln Gly Ile Ala Gly
                 85                  90

<210> SEQ ID NO 34
<211> LENGTH: 90
<212> TYPE: PRT
<213> ORGANISM: Artificial
<220> FEATURE:
<223> OTHER INFORMATION: seq.34
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PNGIAG"can repeat 1 to 10 times, respectively, and the length can
      vary from 9 to 90.

<400> SEQUENCE: 34

Asp Xaa Gly Asp Xaa Gly Asp Xaa Gly Asp Xaa Gly Asp Xaa Gly Asp
 1               5                   10                  15

Xaa Gly Asp Xaa Gly Asp Xaa Gly Asp Xaa Gly Asp Xaa Gly Pro Asn
                20                  25                  30

Gly Ile Ala Gly Pro Asn Gly Ile Ala Gly Pro Asn Gly Ile Ala Gly
         35                  40                  45

Pro Asn Gly Ile Ala Gly Pro Asn Gly Ile Ala Gly Pro Asn Gly Ile
 50                  55                  60

Ala Gly Pro Asn Gly Ile Ala Gly Pro Asn Gly Ile Ala Gly Pro Asn
 65                  70                  75                  80

Gly Ile Ala Gly Pro Asn Gly Ile Ala Gly
                 85                  90
```

```
<210> SEQ ID NO 35
<211> LENGTH: 90
<212> TYPE: PRT
<213> ORGANISM: Artificial
<220> FEATURE:
<223> OTHER INFORMATION: seq.35
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PLGIAG"can repeat 1 to 10 times, respectively, and the length
      can vary from 9 to 90.

<400> SEQUENCE: 35

Asp Xaa Gly Asp Xaa Gly Asp Xaa Gly Asp Xaa Gly Asp Xaa Gly Asp
 1               5                  10                  15

Xaa Gly Asp Xaa Gly Asp Xaa Gly Asp Xaa Gly Asp Xaa Gly Pro Leu
             20                  25                  30

Gly Ile Ala Gly Pro Leu Gly Ile Ala Gly Pro Leu Gly Ile Ala Gly
         35                  40                  45

Pro Leu Gly Ile Ala Gly Pro Leu Gly Ile Ala Gly Pro Leu Gly Ile
     50                  55                  60

Ala Gly Pro Leu Gly Ile Ala Gly Pro Leu Gly Ile Ala Gly Pro Leu
 65                  70                  75                  80

Gly Ile Ala Gly Pro Leu Gly Ile Ala Gly
                 85                  90

<210> SEQ ID NO 36
<211> LENGTH: 90
<212> TYPE: PRT
<213> ORGANISM: Artificial
<220> FEATURE:
<223> OTHER INFORMATION: seq.36
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PIGIAG"can repeat 1 to 10 times, respectively, and the length
      can vary from 9 to 90.

<400> SEQUENCE: 36

Asp Xaa Gly Asp Xaa Gly Asp Xaa Gly Asp Xaa Gly Asp Xaa Gly Asp
 1               5                  10                  15

Xaa Gly Asp Xaa Gly Asp Xaa Gly Asp Xaa Gly Asp Xaa Gly Pro Ile
             20                  25                  30

Gly Ile Ala Gly Pro Ile Gly Ile Ala Gly Pro Ile Gly Ile Ala Gly
         35                  40                  45

Pro Ile Gly Ile Ala Gly Pro Ile Gly Ile Ala Gly Pro Ile Gly Ile
     50                  55                  60

Ala Gly Pro Ile Gly Ile Ala Gly Pro Ile Gly Ile Ala Gly Pro Ile
 65                  70                  75                  80

Gly Ile Ala Gly Pro Ile Gly Ile Ala Gly
                 85                  90

<210> SEQ ID NO 37
<211> LENGTH: 90
<212> TYPE: PRT
<213> ORGANISM: Artificial
<220> FEATURE:
<223> OTHER INFORMATION: seq.37
<220> FEATURE:
```

<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PVGIAG"can repeat 1 to 10 times, respectively, and the length can
      vary from 9 to 90.

<400> SEQUENCE: 37

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Val
            20                  25                  30

Gly Ile Ala Gly Pro Val Gly Ile Ala Gly Pro Val Gly Ile Ala Gly
        35                  40                  45

Pro Val Gly Ile Ala Gly Pro Val Gly Ile Ala Gly Pro Val Gly Ile
    50                  55                  60

Ala Gly Pro Val Gly Ile Ala Gly Pro Val Gly Ile Ala Gly Pro Val
65                  70                  75                  80

Gly Ile Ala Gly Pro Val Gly Ile Ala Gly
            85                  90

<210> SEQ ID NO 38
<211> LENGTH: 90
<212> TYPE: PRT
<213> ORGANISM: Artificial
<220> FEATURE:
<223> OTHER INFORMATION: seq.38
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PAGIAG"can repeat 1 to 10 times, respectively, and the length can
      vary from 9 to 90.

<400> SEQUENCE: 38

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Ala
            20                  25                  30

Gly Ile Ala Gly Pro Ala Gly Ile Ala Gly Pro Ala Gly Ile Ala Gly
        35                  40                  45

Pro Ala Gly Ile Ala Gly Pro Ala Gly Ile Ala Gly Pro Ala Gly Ile
    50                  55                  60

Ala Gly Pro Ala Gly Ile Ala Gly Pro Ala Gly Ile Ala Gly Pro Ala
65                  70                  75                  80

Gly Ile Ala Gly Pro Ala Gly Ile Ala Gly
            85                  90

<210> SEQ ID NO 39
<211> LENGTH: 90
<212> TYPE: PRT
<213> ORGANISM: Artificial
<220> FEATURE:
<223> OTHER INFORMATION: seq.39
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PQGLAG"can repeat 1 to 10 times, respectively, and the length
      can vary from 9 to 90.

<400> SEQUENCE: 39

```
Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Gln
            20                  25                  30

Gly Leu Ala Gly Pro Gln Gly Leu Ala Gly Pro Gln Gly Leu Ala Gly
        35                  40                  45

Pro Gln Gly Leu Ala Gly Pro Gln Gly Leu Ala Gly Pro Gln Gly Leu
    50                  55                  60

Ala Gly Pro Gln Gly Leu Ala Gly Pro Gln Gly Leu Ala Gly Pro Gln
65                  70                  75                  80

Gly Leu Ala Gly Pro Gln Gly Leu Ala Gly
                85                  90
```

<210> SEQ ID NO 40
<211> LENGTH: 90
<212> TYPE: PRT
<213> ORGANISM: Artificial
<220> FEATURE:
<223> OTHER INFORMATION: seq.40
<220> FEATURE:
<221> NAME/KEY: MISC_FEATURE
<222> LOCATION: (1)..(90)
<223> OTHER INFORMATION: A synthesized peptide oligomer for producing a collagen-like polypeptide, wherein X presents Hyp. "DXG" and "PLGLAG"can repeat 1 to 10 times, respectively, and the length can vary from 9 to 90.

<400> SEQUENCE: 40

```
Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Asn
            20                  25                  30

Gly Leu Ala Gly Pro Asn Gly Leu Ala Gly Pro Asn Gly Leu Ala Gly
        35                  40                  45

Pro Asn Gly Leu Ala Gly Pro Asn Gly Leu Ala Gly Pro Asn Gly Leu
    50                  55                  60

Ala Gly Pro Asn Gly Leu Ala Gly Pro Asn Gly Leu Ala Gly Pro Asn
65                  70                  75                  80

Gly Leu Ala Gly Pro Asn Gly Leu Ala Gly
                85                  90
```

<210> SEQ ID NO 41
<211> LENGTH: 90
<212> TYPE: PRT
<213> ORGANISM: Artificial
<220> FEATURE:
<223> OTHER INFORMATION: seq.41
<220> FEATURE:
<221> NAME/KEY: MISC_FEATURE
<222> LOCATION: (1)..(90)
<223> OTHER INFORMATION: A synthesized peptide oligomer for producing a collagen-like polypeptide, wherein X presents Hyp. "DXG" and "PIGLAG"can repeat 1 to 10 times, respectively, and the length can vary from 9 to 90.

<400> SEQUENCE: 41

```
Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Leu
            20                  25                  30

Gly Leu Ala Gly Pro Leu Gly Leu Ala Gly Pro Leu Gly Leu Ala Gly
        35                  40                  45
```

```
Pro Leu Gly Leu Ala Gly Pro Leu Gly Leu Ala Gly Pro Leu Gly Leu
    50                  55                  60

Ala Gly Pro Leu Gly Leu Ala Gly Pro Leu Gly Leu Ala Gly Pro Leu
65                  70                  75                  80

Gly Leu Ala Gly Pro Leu Gly Leu Ala Gly
                85                  90

<210> SEQ ID NO 42
<211> LENGTH: 90
<212> TYPE: PRT
<213> ORGANISM: Artificial
<220> FEATURE:
<223> OTHER INFORMATION: seq.42
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PIGLAG"can repeat 1 to 10 times, respectively, and the length
      can vary from 9 to 90.

<400> SEQUENCE: 42

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Ile
                20                  25                  30

Gly Leu Ala Gly Pro Ile Gly Leu Ala Gly Pro Ile Gly Leu Ala Gly
            35                  40                  45

Pro Ile Gly Leu Ala Gly Pro Ile Gly Leu Ala Gly Pro Ile Gly Leu
    50                  55                  60

Ala Gly Pro Ile Gly Leu Ala Gly Pro Ile Gly Leu Ala Gly Pro Ile
65                  70                  75                  80

Gly Leu Ala Gly Pro Ile Gly Leu Ala Gly
                85                  90

<210> SEQ ID NO 43
<211> LENGTH: 90
<212> TYPE: PRT
<213> ORGANISM: Artificial
<220> FEATURE:
<223> OTHER INFORMATION: seq.43
<220> FEATURE:
<221> NAME/KEY: MISC_FEATURE
<222> LOCATION: (1)..(90)
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PVGLAG"can repeat 1 to 10 times, respectively, and the length can
      vary from 9 to 90.

<400> SEQUENCE: 43

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Val
                20                  25                  30

Gly Leu Ala Gly Pro Val Gly Leu Ala Gly Pro Val Gly Leu Ala Gly
            35                  40                  45

Pro Val Gly Leu Ala Gly Pro Val Gly Leu Ala Gly Pro Val Gly Leu
    50                  55                  60

Ala Gly Pro Val Gly Leu Ala Gly Pro Val Gly Leu Ala Gly Pro Val
65                  70                  75                  80
```

```
Gly Leu Ala Gly Pro Val Gly Leu Ala Gly
            85                  90

<210> SEQ ID NO 44
<211> LENGTH: 90
<212> TYPE: PRT
<213> ORGANISM: Artificial
<220> FEATURE:
<223> OTHER INFORMATION: seq.44
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "DXG" and
      "PAGLAG"can repeat 1 to 10 times, respectively, and the length can
      vary from 9 to 90.

<400> SEQUENCE: 44

Asp Xaa Gly Asp Xaa Gly Asp Xaa Gly Asp Xaa Gly Asp Xaa Gly Asp
1               5                   10                  15

Xaa Gly Asp Xaa Gly Asp Xaa Gly Asp Xaa Gly Asp Xaa Gly Pro Ala
            20                  25                  30

Gly Leu Ala Gly Pro Ala Gly Leu Ala Gly Pro Ala Gly Leu Ala Gly
        35                  40                  45

Pro Ala Gly Leu Ala Gly Pro Ala Gly Leu Ala Gly Pro Ala Gly Leu
    50                  55                  60

Ala Gly Pro Ala Gly Leu Ala Gly Pro Ala Gly Leu Ala Gly Pro Ala
65                  70                  75                  80

Gly Leu Ala Gly Pro Ala Gly Leu Ala Gly
            85                  90

<210> SEQ ID NO 45
<211> LENGTH: 90
<212> TYPE: PRT
<213> ORGANISM: Artificial
<220> FEATURE:
<223> OTHER INFORMATION: seq.45
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PQGIAG"can repeat 1
      to 10 times, respectively, and the length can vary from 9 to 90.

<400> SEQUENCE: 45

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Gln
            20                  25                  30

Gly Ile Ala Gly Pro Gln Gly Ile Ala Gly Pro Gln Gly Ile Ala Gly
        35                  40                  45

Pro Gln Gly Ile Ala Gly Pro Gln Gly Ile Ala Gly Pro Gln Gly Ile
    50                  55                  60

Ala Gly Pro Gln Gly Ile Ala Gly Pro Gln Gly Ile Ala Gly Pro Gln
65                  70                  75                  80

Gly Ile Ala Gly Pro Gln Gly Ile Ala Gly
            85                  90

<210> SEQ ID NO 46
<211> LENGTH: 90
<212> TYPE: PRT
<213> ORGANISM: Artificial
<220> FEATURE:
<223> OTHER INFORMATION: seq.46
```

-continued

```
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PNGIAG"can repeat 1
      to 10 times, respectively, and the length can vary from 9 to 90.

<400> SEQUENCE: 46

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Asn
            20                  25                  30

Gly Ile Ala Gly Pro Asn Gly Ile Ala Gly Pro Asn Gly Ile Ala Gly
        35                  40                  45

Pro Asn Gly Ile Ala Gly Pro Asn Gly Ile Ala Gly Pro Asn Gly Ile
    50                  55                  60

Ala Gly Pro Asn Gly Ile Ala Gly Pro Asn Gly Ile Ala Gly Pro Asn
65                  70                  75                  80

Gly Ile Ala Gly Pro Asn Gly Ile Ala Gly
                85                  90

<210> SEQ ID NO 47
<211> LENGTH: 90
<212> TYPE: PRT
<213> ORGANISM: Artificial
<220> FEATURE:
<223> OTHER INFORMATION: seq.47
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PLGIAG"can repeat 1
      to 10 times, respectively, and the length can vary from 9 to 90.

<400> SEQUENCE: 47

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Leu
            20                  25                  30

Gly Ile Ala Gly Pro Leu Gly Ile Ala Gly Pro Leu Gly Ile Ala Gly
        35                  40                  45

Pro Leu Gly Ile Ala Gly Pro Leu Gly Ile Ala Gly Pro Leu Gly Ile
    50                  55                  60

Ala Gly Pro Leu Gly Ile Ala Gly Pro Leu Gly Ile Ala Gly Pro Leu
65                  70                  75                  80

Gly Ile Ala Gly Pro Leu Gly Ile Ala Gly
                85                  90

<210> SEQ ID NO 48
<211> LENGTH: 90
<212> TYPE: PRT
<213> ORGANISM: Artificial
<220> FEATURE:
<223> OTHER INFORMATION: seq.48
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EPG" and
      "PIGIAG"can repeat 1 to 10 times, respectively, and the length
      can vary from 9 to 90.

<400> SEQUENCE: 48

Glu Pro Gly Glu Pro Gly Glu Pro Gly Glu Pro Gly Glu Pro Gly Glu
```

```
1               5                   10                  15
Pro Gly Glu Pro Gly Glu Pro Gly Glu Pro Gly Glu Pro Gly Pro Ile
                20                  25                  30

Gly Ile Ala Gly Pro Ile Gly Ile Ala Gly Pro Ile Gly Ile Ala Gly
            35                  40                  45

Pro Ile Gly Ile Ala Gly Pro Ile Gly Ile Ala Gly Pro Ile Gly Ile
        50                  55                  60

Ala Gly Pro Ile Gly Ile Ala Gly Pro Ile Gly Ile Ala Gly Pro Ile
65                  70                  75                  80

Gly Ile Ala Gly Pro Ile Gly Ile Ala Gly
                85                  90

<210> SEQ ID NO 49
<211> LENGTH: 90
<212> TYPE: PRT
<213> ORGANISM: Artificial
<220> FEATURE:
<223> OTHER INFORMATION: seq.49
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PVGIAG"can repeat 1
      to 10 times, respectively, and the length can vary from 9 to 90.

<400> SEQUENCE: 49

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Val
                20                  25                  30

Gly Ile Ala Gly Pro Val Gly Ile Ala Gly Pro Val Gly Ile Ala Gly
            35                  40                  45

Pro Val Gly Ile Ala Gly Pro Val Gly Ile Ala Gly Pro Val Gly Ile
        50                  55                  60

Ala Gly Pro Val Gly Ile Ala Gly Pro Val Gly Ile Ala Gly Pro Val
65                  70                  75                  80

Gly Ile Ala Gly Pro Val Gly Ile Ala Gly
                85                  90

<210> SEQ ID NO 50
<211> LENGTH: 90
<212> TYPE: PRT
<213> ORGANISM: Artificial
<220> FEATURE:
<223> OTHER INFORMATION: seq.50
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PAGIAG"can repeat 1
      to 10 times, respectively, and the length can vary from 9 to 90.

<400> SEQUENCE: 50

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Ala
                20                  25                  30

Gly Ile Ala Gly Pro Ala Gly Ile Ala Gly Pro Ala Gly Ile Ala Gly
            35                  40                  45

Pro Ala Gly Ile Ala Gly Pro Ala Gly Ile Ala Gly Pro Ala Gly Ile
        50                  55                  60
```

Ala Gly Pro Ala Gly Ile Ala Gly Pro Ala Gly Ile Ala Gly Pro Ala
65                  70                  75                  80

Gly Ile Ala Gly Pro Ala Gly Ile Ala Gly
                85                  90

<210> SEQ ID NO 51
<211> LENGTH: 90
<212> TYPE: PRT
<213> ORGANISM: Artificial
<220> FEATURE:
<223> OTHER INFORMATION: seq.51
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PQGLAG"can repeat 1
      to 10 times, respectively, and the length can vary from 9 to 90.

<400> SEQUENCE: 51

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Gln
                20                  25                  30

Gly Leu Ala Gly Pro Gln Gly Leu Ala Gly Pro Gln Gly Leu Ala Gly
            35                  40                  45

Pro Gln Gly Leu Ala Gly Pro Gln Gly Leu Ala Gly Pro Gln Gly Leu
        50                  55                  60

Ala Gly Pro Gln Gly Leu Ala Gly Pro Gln Gly Leu Ala Gly Pro Gln
65                  70                  75                  80

Gly Leu Ala Gly Pro Gln Gly Leu Ala Gly
                85                  90

<210> SEQ ID NO 52
<211> LENGTH: 90
<212> TYPE: PRT
<213> ORGANISM: Artificial
<220> FEATURE:
<223> OTHER INFORMATION: seq.52
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PNGLAG"can repeat 1
      to 10 times, respectively, and the length can vary from 9 to 90.

<400> SEQUENCE: 52

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Asn
                20                  25                  30

Gly Leu Ala Gly Pro Asn Gly Leu Ala Gly Pro Asn Gly Leu Ala Gly
            35                  40                  45

Pro Asn Gly Leu Ala Gly Pro Asn Gly Leu Ala Gly Pro Asn Gly Leu
        50                  55                  60

Ala Gly Pro Asn Gly Leu Ala Gly Pro Asn Gly Leu Ala Gly Pro Asn
65                  70                  75                  80

Gly Leu Ala Gly Pro Asn Gly Leu Ala Gly
                85                  90

<210> SEQ ID NO 53
<211> LENGTH: 90
<212> TYPE: PRT
<213> ORGANISM: Artificial

<220> FEATURE:
<223> OTHER INFORMATION: seq.53
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PLGLAG"can repeat 1
      to 10 times, respectively, and the length can vary from 9 to 90.

<400> SEQUENCE: 53

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Leu
            20                  25                  30

Gly Leu Ala Gly Pro Leu Gly Leu Ala Gly Pro Leu Gly Leu Ala Gly
        35                  40                  45

Pro Leu Gly Leu Ala Gly Pro Leu Gly Leu Ala Gly Pro Leu Gly Leu
    50                  55                  60

Ala Gly Pro Leu Gly Leu Ala Gly Pro Leu Gly Leu Ala Gly Pro Leu
65                  70                  75                  80

Gly Leu Ala Gly Pro Leu Gly Leu Ala Gly
                85                  90

<210> SEQ ID NO 54
<211> LENGTH: 90
<212> TYPE: PRT
<213> ORGANISM: Artificial
<220> FEATURE:
<223> OTHER INFORMATION: seq.54
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PIGLAG"can repeat 1
      to 10 times, respectively, and the length can vary from 9 to 90.

<400> SEQUENCE: 54

Glu Pro Gly Glu Pro Gly Glu Pro Gly Glu Pro Gly Glu Pro Gly Glu
1               5                   10                  15

Pro Gly Glu Pro Gly Glu Pro Gly Glu Pro Gly Glu Pro Gly Pro Ile
            20                  25                  30

Gly Leu Ala Gly Pro Ile Gly Leu Ala Gly Pro Ile Gly Leu Ala Gly
        35                  40                  45

Pro Ile Gly Leu Ala Gly Pro Ile Gly Leu Ala Gly Pro Ile Gly Leu
    50                  55                  60

Ala Gly Pro Ile Gly Leu Ala Gly Pro Ile Gly Leu Ala Gly Pro Ile
65                  70                  75                  80

Gly Leu Ala Gly Pro Ile Gly Leu Ala Gly
                85                  90

<210> SEQ ID NO 55
<211> LENGTH: 90
<212> TYPE: PRT
<213> ORGANISM: Artificial
<220> FEATURE:
<223> OTHER INFORMATION: seq.55
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PVGLAG"can repeat 1
      to 10 times, respectively, and the length can vary from 9 to 90.

<400> SEQUENCE: 55

```
Glu Pro Gly Glu Pro Gly Glu Pro Gly Glu Pro Gly Glu
1               5                   10                  15

Pro Gly Glu Pro Gly Glu Pro Gly Glu Pro Gly Pro Val
            20                  25                  30

Gly Leu Ala Gly Pro Val Gly Leu Ala Gly Pro Val Gly Leu Ala Gly
        35                  40                  45

Pro Val Gly Leu Ala Gly Pro Val Gly Leu Ala Gly Pro Val Gly Leu
    50                  55                  60

Ala Gly Pro Val Gly Leu Ala Gly Pro Val Gly Leu Ala Gly Pro Val
65              70                  75                  80

Gly Leu Ala Gly Pro Val Gly Leu Ala Gly
            85                  90
```

<210> SEQ ID NO 56
<211> LENGTH: 90
<212> TYPE: PRT
<213> ORGANISM: Artificial
<220> FEATURE:
<223> OTHER INFORMATION: seq.56
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein "EPG" and "PAGLAG"can repeat 1
      to 10 times, respectively, and the length can vary from 9 to 90.

<400> SEQUENCE: 56

```
Glu Pro Gly Glu Pro Gly Glu Pro Gly Glu Pro Gly Glu
1               5                   10                  15

Pro Gly Glu Pro Gly Glu Pro Gly Glu Pro Gly Pro Ala
            20                  25                  30

Gly Leu Ala Gly Pro Ala Gly Leu Ala Gly Pro Ala Gly Leu Ala Gly
        35                  40                  45

Pro Ala Gly Leu Ala Gly Pro Ala Gly Leu Ala Gly Pro Ala Gly Leu
    50                  55                  60

Ala Gly Pro Ala Gly Leu Ala Gly Pro Ala Gly Leu Ala Gly Pro Ala
65              70                  75                  80

Gly Leu Ala Gly Pro Ala Gly Leu Ala Gly
            85                  90
```

<210> SEQ ID NO 57
<211> LENGTH: 90
<212> TYPE: PRT
<213> ORGANISM: Artificial
<220> FEATURE:
<223> OTHER INFORMATION: seq.57
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PQGIAG"can repeat 1 to 10 times, respectively, and the length can
      vary from 9 to 90.

<400> SEQUENCE: 57

```
Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Gln
            20                  25                  30

Gly Ile Ala Gly Pro Gln Gly Ile Ala Gly Pro Gln Gly Ile Ala Gly
        35                  40                  45

Pro Gln Gly Ile Ala Gly Pro Gln Gly Ile Ala Gly Pro Gln Gly Ile
```

```
                     50                  55                  60
Ala Gly Pro Gln Gly Ile Ala Gly Pro Gln Gly Ile Ala Gly Pro Gln
 65                  70                  75                  80

Gly Ile Ala Gly Pro Gln Gly Ile Ala Gly
                 85                  90

<210> SEQ ID NO 58
<211> LENGTH: 90
<212> TYPE: PRT
<213> ORGANISM: Artificial
<220> FEATURE:
<223> OTHER INFORMATION: seq.58
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PNGIAG"can repeat 1 to 10 times, respectively, and the length
      can vary from 9 to 90.

<400> SEQUENCE: 58

Glu Xaa Gly Glu Xaa Gly Glu Xaa Gly Glu Xaa Gly Glu Xaa Gly Glu
 1               5                  10                  15

Xaa Gly Glu Xaa Gly Glu Xaa Gly Glu Xaa Gly Glu Xaa Gly Pro Asn
                 20                  25                  30

Gly Ile Ala Gly Pro Asn Gly Ile Ala Gly Pro Asn Gly Ile Ala Gly
             35                  40                  45

Pro Asn Gly Ile Ala Gly Pro Asn Gly Ile Ala Gly Pro Asn Gly Ile
         50                  55                  60

Ala Gly Pro Asn Gly Ile Ala Gly Pro Asn Gly Ile Ala Gly Pro Asn
 65                  70                  75                  80

Gly Ile Ala Gly Pro Asn Gly Ile Ala Gly
                 85                  90

<210> SEQ ID NO 59
<211> LENGTH: 90
<212> TYPE: PRT
<213> ORGANISM: Artificial
<220> FEATURE:
<223> OTHER INFORMATION: seq.59
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PLGIAG"can repeat 1 to 10 times, respectively, and the length can
      vary from 9 to 90.

<400> SEQUENCE: 59

Glu Xaa Gly Glu Xaa Gly Glu Xaa Gly Glu Xaa Gly Glu Xaa Gly Glu
 1               5                  10                  15

Xaa Gly Glu Xaa Gly Glu Xaa Gly Glu Xaa Gly Glu Xaa Gly Pro Leu
                 20                  25                  30

Gly Ile Ala Gly Pro Leu Gly Ile Ala Gly Pro Leu Gly Ile Ala Gly
             35                  40                  45

Pro Leu Gly Ile Ala Gly Pro Leu Gly Ile Ala Gly Pro Leu Gly Ile
         50                  55                  60

Ala Gly Pro Leu Gly Ile Ala Gly Pro Leu Gly Ile Ala Gly Pro Leu
 65                  70                  75                  80

Gly Ile Ala Gly Pro Leu Gly Ile Ala Gly
                 85                  90
```

```
<210> SEQ ID NO 60
<211> LENGTH: 90
<212> TYPE: PRT
<213> ORGANISM: Artificial
<220> FEATURE:
<223> OTHER INFORMATION: seq.60
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PIGIAG"can repeat 1 to 10 times, respectively, and the length
      can vary from 9 to 90.

<400> SEQUENCE: 60

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Ile
            20                  25                  30

Gly Ile Ala Gly Pro Ile Gly Ile Ala Gly Pro Ile Gly Ile Ala Gly
        35                  40                  45

Pro Ile Gly Ile Ala Gly Pro Ile Gly Ile Ala Gly Pro Ile Gly Ile
    50                  55                  60

Ala Gly Pro Ile Gly Ile Ala Gly Pro Ile Gly Ile Ala Gly Pro Ile
65                  70                  75                  80

Gly Ile Ala Gly Pro Ile Gly Ile Ala Gly
                85                  90

<210> SEQ ID NO 61
<211> LENGTH: 90
<212> TYPE: PRT
<213> ORGANISM: Artificial
<220> FEATURE:
<223> OTHER INFORMATION: seq.61
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PVGIAG"can repeat 1 to 10 times, respectively, and the length can
      vary from 9 to 90.

<400> SEQUENCE: 61

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Val
            20                  25                  30

Gly Ile Ala Gly Pro Val Gly Ile Ala Gly Pro Val Gly Ile Ala Gly
        35                  40                  45

Pro Val Gly Ile Ala Gly Pro Val Gly Ile Ala Gly Pro Val Gly Ile
    50                  55                  60

Ala Gly Pro Val Gly Ile Ala Gly Pro Val Gly Ile Ala Gly Pro Val
65                  70                  75                  80

Gly Ile Ala Gly Pro Val Gly Ile Ala Gly
                85                  90

<210> SEQ ID NO 62
<211> LENGTH: 90
<212> TYPE: PRT
<213> ORGANISM: Artificial
<220> FEATURE:
<223> OTHER INFORMATION: seq.62
<220> FEATURE:
<221> NAME/KEY: MISC_FEATURE
<222> LOCATION: (1)..(90)
```

```
<223> OTHER INFORMATION: A synthesized peptide oligomer for producing a
      collagen-like polypeptide, wherein X presents Hyp. "EXG" and
      "PAGIAG"can repeat 1 to 10 times, respectively, and the length can
      vary from 9 to 90.

<400> SEQUENCE: 62

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Ala
            20                  25                  30

Gly Ile Ala Gly Pro Ala Gly Ile Ala Gly Pro Ala Gly Ile Ala Gly
        35                  40                  45

Pro Ala Gly Ile Ala Gly Pro Ala Gly Ile Ala Gly Pro Ala Gly Ile
    50                  55                  60

Ala Gly Pro Ala Gly Ile Ala Gly Pro Ala Gly Ile Ala Gly Pro Ala
65                  70                  75                  80

Gly Ile Ala Gly Pro Ala Gly Ile Ala Gly
                85                  90

<210> SEQ ID NO 63
<211> LENGTH: 90
<212> TYPE: PRT
<213> ORGANISM: Artificial
<220> FEATURE:
<223> OTHER INFORMATION: seq.63
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PQGLAG"can repeat 1 to 10 times, respectively, and the length
      can vary from 9 to 90.

<400> SEQUENCE: 63

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Gln
            20                  25                  30

Gly Leu Ala Gly Pro Gln Gly Leu Ala Gly Pro Gln Gly Leu Ala Gly
        35                  40                  45

Pro Gln Gly Leu Ala Gly Pro Gln Gly Leu Ala Gly Pro Gln Gly Leu
    50                  55                  60

Ala Gly Pro Gln Gly Leu Ala Gly Pro Gln Gly Leu Ala Gly Pro Gln
65                  70                  75                  80

Gly Leu Ala Gly Pro Gln Gly Leu Ala Gly
                85                  90

<210> SEQ ID NO 64
<211> LENGTH: 90
<212> TYPE: PRT
<213> ORGANISM: Artificial
<220> FEATURE:
<223> OTHER INFORMATION: seq.64
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PNGLAG"can repeat 1 to 10 times, respectively, and the length
      can vary from 9 to 90.
```

<400> SEQUENCE: 64

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Asn
            20                  25                  30

Gly Leu Ala Gly Pro Asn Gly Leu Ala Gly Pro Asn Gly Leu Ala Gly
            35                  40                  45

Pro Asn Gly Leu Ala Gly Pro Asn Gly Leu Ala Gly Pro Asn Gly Leu
        50                  55                  60

Ala Gly Pro Asn Gly Leu Ala Gly Pro Asn Gly Leu Ala Gly Pro Asn
65                  70                  75                  80

Gly Leu Ala Gly Pro Asn Gly Leu Ala Gly
                85                  90

<210> SEQ ID NO 65
<211> LENGTH: 90
<212> TYPE: PRT
<213> ORGANISM: Artificial
<220> FEATURE:
<223> OTHER INFORMATION: seq.65
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PLGLAG"can repeat 1 to 10 times, respectively, and the length
      can vary from 9 to 90.

<400> SEQUENCE: 65

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Leu
            20                  25                  30

Gly Leu Ala Gly Pro Leu Gly Leu Ala Gly Pro Leu Gly Leu Ala Gly
            35                  40                  45

Pro Leu Gly Leu Ala Gly Pro Leu Gly Leu Ala Gly Pro Leu Gly Leu
        50                  55                  60

Ala Gly Pro Leu Gly Leu Ala Gly Pro Leu Gly Leu Ala Gly Pro Leu
65                  70                  75                  80

Gly Leu Ala Gly Pro Leu Gly Leu Ala Gly
                85                  90

<210> SEQ ID NO 66
<211> LENGTH: 90
<212> TYPE: PRT
<213> ORGANISM: Artificial
<220> FEATURE:
<223> OTHER INFORMATION: seq.66
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PIGLAG"can repeat 1 to 10 times, respectively, and the length
      can vary from 9 to 90.

<400> SEQUENCE: 66

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Ile
            20                  25                  30

```
Gly Leu Ala Gly Pro Ile Gly Leu Ala Gly Pro Ile Gly Leu Ala Gly
            35                  40                  45

Pro Ile Gly Leu Ala Gly Pro Ile Gly Leu Ala Gly Pro Ile Gly Leu
        50                  55                  60

Ala Gly Pro Ile Gly Leu Ala Gly Pro Ile Gly Leu Ala Gly Pro Ile
65                  70                  75                  80

Gly Leu Ala Gly Pro Ile Gly Leu Ala Gly
                85                  90

<210> SEQ ID NO 67
<211> LENGTH: 90
<212> TYPE: PRT
<213> ORGANISM: Artificial
<220> FEATURE:
<223> OTHER INFORMATION: seq.67
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PVGLAG"can repeat 1 to 10 times, respectively, and the length
      can vary from 9 to 90.

<400> SEQUENCE: 67

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Val
            20                  25                  30

Gly Leu Ala Gly Pro Val Gly Leu Ala Gly Pro Val Gly Leu Ala Gly
            35                  40                  45

Pro Val Gly Leu Ala Gly Pro Val Gly Leu Ala Gly Pro Val Gly Leu
        50                  55                  60

Ala Gly Pro Val Gly Leu Ala Gly Pro Val Gly Leu Ala Gly Pro Val
65                  70                  75                  80

Gly Leu Ala Gly Pro Val Gly Leu Ala Gly
                85                  90

<210> SEQ ID NO 68
<211> LENGTH: 90
<212> TYPE: PRT
<213> ORGANISM: Artificial
<220> FEATURE:
<223> OTHER INFORMATION: seq.68
<220> FEATURE:
<221> NAME/KEY: MISC_FEATURE
<222> LOCATION: (1)..(90)
<223> OTHER INFORMATION: A synthesized peptide oligomer for producing a
      collagen-like polypeptide, wherein X presents Hyp. "EXG" and
      "PAGLAG"can repeat 1 to 10 times, respectively, and the length
      can vary from 9 to 90.

<400> SEQUENCE: 68

Glu Xaa Gly Glu Xaa Gly Glu Xaa Gly Glu Xaa Gly Glu Xaa Gly Glu
1               5                   10                  15

Xaa Gly Glu Xaa Gly Glu Xaa Gly Glu Xaa Gly Glu Xaa Gly Pro Ala
            20                  25                  30

Gly Leu Ala Gly Pro Ala Gly Leu Ala Gly Pro Ala Gly Leu Ala Gly
            35                  40                  45

Pro Ala Gly Leu Ala Gly Pro Ala Gly Leu Ala Gly Pro Ala Gly Leu
        50                  55                  60
```

-continued

```
Ala Gly Pro Ala Gly Leu Ala Gly Pro Ala Gly Leu Ala Gly Pro Ala
65                  70                  75                  80

Gly Leu Ala Gly Pro Ala Gly Leu Ala Gly
                85                  90
```